United States Patent [19]

Huang et al.

[11] Patent Number: 5,360,910

[45] Date of Patent: Nov. 1, 1994

[54] PESTICIDAL 1-ARYL-5-(SUBSTITUTED ALKYLIDENEIMINO)PYRAZOLES

[75] Inventors: Jamin Huang, Chapel Hill; Hafez M. Ayad, Cary; Philip R. Timmons, Durham, all of N.C.

[73] Assignee: Rhone-Poulenc AG Company, Research Triangle Park, N.C.

[21] Appl. No.: 842,431

[22] Filed: Mar. 4, 1992

Related U.S. Application Data

[63] Continuation-in-part of Ser. No. 790,449, Nov. 12, 1991, abandoned, which is a continuation-in-part of Ser. No. 693,580, Apr. 30, 1991, Pat. No. 5,236,938.

[51] Int. Cl.[5] .......................................... C07D 401/14
[52] U.S. Cl. .................................. 546/279; 548/255; 548/266.6; 548/312.4; 548/365.1; 548/365.7; 548/367.7; 548/371.7; 548/372.1; 548/372.5
[58] Field of Search ............ 548/376, 378, 255, 266.6, 548/336; 514/407; 546/279

[56] References Cited

U.S. PATENT DOCUMENTS

| | | | |
|---|---|---|---|
| 2,998,419 | 8/1961 | Dickenson et al. | 260/240 |
| 3,686,171 | 8/1972 | Swett et al. | 260/240 |
| 4,685,957 | 8/1987 | Gehring et al. | 71/92 |
| 4,740,232 | 4/1988 | Gehring et al. | 71/92 |
| 4,772,312 | 9/1988 | Schallner et al. | 71/92 |
| 4,804,675 | 2/1989 | Jensen-Korte et al. | 514/407 |
| 4,822,810 | 4/1989 | Lindig et al. | 514/407 |
| 4,863,937 | 9/1989 | Gehring et al. | 514/333 |

FOREIGN PATENT DOCUMENTS

| | | |
|---|---|---|
| 301339 | 7/1988 | European Pat. Off. |
| 295117 | 12/1988 | European Pat. Off. |
| 295118 | 12/1988 | European Pat. Off. |
| 923734 | 4/1963 | United Kingdom |
| 87/03781 | 7/1987 | World Int. Prop. O. |

OTHER PUBLICATIONS

Chem. Abstr. 113(25):23164g Corresponding to J. Prakt. Chem. 332(3), 351–8, Hennig L. et al.

Acta Chimica Academiae Scientiarum Hungaricae, Tomus 105(2), 127–139 (1980), Simay, T., et al.

*Primary Examiner*—C. Warren Ivy
*Assistant Examiner*—A. A. Owens
*Attorney, Agent, or Firm*—Morgan & Finnegan

[57] ABSTRACT

The invention describes novel 1-aryl-5-(substituted alkylideneimino)pyrazoles of formula (I)

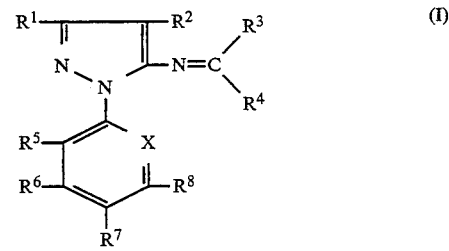

wherein typically preferred substituents are:

$R^1$ is cyano, nitro, or halogen;

$R^2$ is $R^9S(O)_n$ in which n is 0, 1 or 2 and $R^9$ is alkyl, preferably methyl which is substituted by halogen atoms which are the same or different up to full substitution of the alkyl moiety;

$R^3$ is hydrogen or alkyl;

$R^4$ is phenyl or heteroaryl, optionally substituted by one or more hydroxy, halogen, alkoxy, alkylthio, cyano or alkyl or combinations thereof; preferably $R^4$ is phenyl, which is at least substituted by 3-hydroxy or 4-hydroxy;

$R^5$ is hydrogen, alkyl or halogen;

$R^6$ and $R^8$ are hydrogen;

$R^7$ is halogen, alkyl, haloalkyl or haloalkoxy; and

X is a nitrogen atom or $CR^{14}$ in which $R^{14}$ is hydrogen, halogen, cyano, alkyl, alkylthio or alkoxy.

The invention further describes processes to make the compounds, compositions of the compounds, and methods of use of the compounds for the control of arthropods (mites, aphids or insects), nematodes, helminths, or protozoa.

2 Claims, No Drawings

PESTICIDAL 1-ARYL-5-(SUBSTITUTED ALKYLIDENEIMINO)PYRAZOLES

This is a continuation in part of copending application Ser. No. 07/790,449, filed Nov. 12, 1991, abandoned which is a continuation in part of copending application Ser. No. 07/693,580, filed Apr. 30, 1991, now U.S. Pat. No. 5,236,938 both of which are incorporated herein by reference.

BACKGROUND OF THE INVENTION

1. Field of the Invention

The invention relates to new 1-aryl-5-(substituted alkylideneimino)pyrazoles and to processes for their preparation. The invention further pertains to compositions of said compounds and methods, using said compounds, for the control of arthropod, nematode, helminth or protozoan pests. In particular it relates to the application of said compounds or compositions in agricultural methods of use, particularly as pesticides, for controlling arthropods, especially insects via ingestion or contact action.

2. Description of the Related Art

Various 1-(substituted phenyl or pyridyl)-5-(substituted amino) pyrazole compounds are known to exhibit a number of different types of pesticidal activity, including activity as herbicides, plant growth regulators, insecticides, and nematicides. Included among these are the following:

U.S. Pat. No. 4,863,937 discloses as insecticides, acaricides and nematicides 1-aryl-5-(substituted alkylideneimino)pyrazoles, which are unsubstituted or alkyl or haloalkyl substituted in the 3-position of the pyrazole ring;

EP 301,339 and corresponding CAS reference 111(5):39360c disclose 1-(substituted aryl)-5-(substituted aryl methylideneimino)pyrazole compounds- (per pages 3, 6, 10 and 16 of the reference) as intermediates to insecticidal compounds. The compounds are unsubstituted or alkyl or haloalkyl substituted in the 3-position of the pyrazole ring;

J. Prakt. Chem., 332(3), 351–8, 1990, Hennig L. et al., corresponding to CAS reference 113 (25):231264 g, is a chemistry article which discloses 1-phenyl-5-(substituted phenyl methylideneimino) pyrazole compounds, which are either methyl or phenyl substituted in the 3-position of the pyrazole ring. There appears to be no disclosed pesticidal activity;

GB 923,734 discloses 1-aryl-5-(substituted phenyl methylideneimino)pyrazole compounds as dyes and which are only substituted by cyano in the 3-position of the pyrazole ring;

U.S. Pat. No. 4,685,957 discloses 1-aryl-5-(substituted iminoamino)pyrazoles as herbicides and plant growth regulators, which compounds are unsubstituted or alkyl substituted in the 3-position of the pyrazole ring;

EP 295,117; WO 87/03781 (also corresponding to EP 234,119); EP 295, 118; and EP 350,311 disclose 1-phenyl-5-(substituted amino)pyrazole compounds for control of arthropod, nematode, helminth and protozoan pests;

GB 2,136,427 discloses as herbicides 1-(substituted-2-pyridyl)-5-(substituted amino)-4-cyanopyrazoles, which are unsubstituted at the 3-position of the pyrazole ring;

U.S. Pat. No. 4,772,312 discloses as herbicides 1-(substituted-2-pyridyl)-5-(substituted amino)pyrazoles, which are unsubstituted or alkyl substituted in the 3-position of the pyrazole ring;

U.S. Pat. No. 4,804,675 discloses as insecticides, acaricides, and nematicides 1-(substituted-2-pyridyl)-5-(substituted amino)pyrazoles, which are unsubstituted or alkyl or haloalkyl substituted in the 3-position of the pyrazole ring;

U.S. Pat. No. 4,740,232 discloses as herbicides 1-(substituted phenyl)-5-(substituted amino)pyrazole compounds, which are unsubstituted in the 3-position of the pyrazole ring;

EP 398,499 discloses phenyl substituted heterocyclic compounds as insecticides and acaricides, including 1-(substituted phenyl)-5-(substituted amino)pyrazoles.

U.S. Pat. No. 4,822,810 discloses 1-aryl-4-cyano-3-(sulfur substituted)-5-(alkoxyalkylideneimino)pyrazoles for the control of arthropod pests.

U.S. Pat. No. 3,686,171 discloses N'-[(4-hydroxymethyl or formyl)-5-pyrazolyl]amidines as intermediates or anti-inflammatory agents.

U.S. Pat. No. 2,998,419 discloses the process of manufacture and use of affinity for proteins of 5-(substituted amino)-3,4-dicyanopyrazoles.

Acta Chimica Academiae Scientiarum Hungaricae, Tomus 105(2), 127–139 (1980), Simay, T. et al., discloses the chemical synthesis and physical properties of various 5-(substituted amino)pyrazoles (for examples compounds 2, 4, 7, 8 and 15–18).

It is thus apparent that the nature and position of substituent groups on a pyrazole ring provide widely different types of biological activity which type and level of activity is not readily apparent.

SUMMARY OF THE INVENTION

The present invention pertains to novel 1-aryl-5-(substituted alkylideneimino)pyrazoles which exhibit surprising, unexpected and excellent pesticidal properties, especially as insecticides for control via ingestion or contact action.

The compounds including their isomers, e.g. diastero and optical isomers, are compounds of a general formula (I)

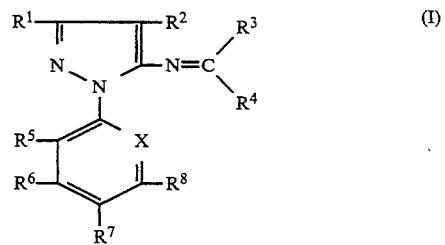

wherein:

$R^1$ is cyano, nitro, halogen:, formyl, alkylcarbonyl or cycloalkylcarbonyl; and wherein the alkyl moieties are linear or branched chains of 1–4 carbon atoms and the cycloalkyl moiety contains 3 to 7 carbon atoms;

$R^2$ is: halogen; alkyl; haloalkyl; alkoxy; haloalkoxy; nitro; thiocyanato; unsubstituted or mono- or dialkyl substituted sulfanoyl; unsubstituted or mono- or dialkyl substituted aminocarbonyl; alkoxycarbonyl; or unsubstituted or substituted $R^9S(O)_n$, in which n is 0, 1 or 2 and $R^9$ is alkyl, haloalkyl, cycloalkyl, halocycloalkyl, cycloalkylalkyl or halocycloalkylalkyl; and wherein the alkyl moieties are linear or branched chains of 1–4 carbon atoms, the cycloalkyl moiety contains 3 to 7 carbon atoms and the halo substitution consists of one or more halogen atoms, which are the same or different, up to full substitution of the alkyl and cycloalkyl moieties;

$R^3$ is hydrogen, $C_{1-4}$ alkyl, $C_{1-4}$ alkoxy, $C_{1-4}$ alkylthio or di-$C_{1-4}$ alkylamino; and wherein the alkyl moieties are linear or branched chains;

$R^4$ is unsubstituted or substituted phenyl or unsubstituted or substituted heteroaryl having a five or six membered monocyclic ring containing one or more of the same or different oxygen, sulfur or nitrogen hetero atoms; and wherein the phenyl or heteroaryl substitution is one or more or combinations of: hydroxy or inorganic or organic salt thereof; sulfhydryl or inorganic or organic salt thereof; halogen; cyano; nitro; alkyl; haloalkyl; alkoxy; -O-alkyl-O-; O-haloalkyl-O-; haloalkoxy; alkanoyloxy; phenoxy; trialkylsilyloxy; phenyl; alkyl-S(O)$_n$ or haloalkyl-S(O)$_n$, in which n is 0, 1 or 2; $NR^{10}R^{11}$ in which $R^{10}$ and $R^{11}$ are individually hydrogen, alkyl, alkanoyl or haloalkanoyl; $COR^{12}$ in which $R^{12}$ is $NR^{10}R^{11}$, alkoxy, alkylthio, hydroxy or inorganic or organic salt thereof, hydrogen, alkyl or haloalkyl; or $SO_2R^{13}$ in which $R^{13}$ is $NR^{10}R^{11}$, alkoxy, alkylthio, or hydroxy or inorganic or organic salt thereof; and wherein the alkyl and alkoxy moieties are linear or branched chains of 1-4 carbon atoms and the halo substitution consists of one or more halogen atoms, which are the same or different, up to full substitution of the alkyl and alkoxy moieties;

$R^5$ is hydrogen, halogen or linear or branched chain $C_{1-4}$ alkyl;

$R^6$ and $R^8$ are each individually hydrogen or fluorine;

$R^7$ is halogen, alkyl, haloalkyl, alkoxy, haloalkoxy, cyano, nitro, alkylcarbonyl, haloalkylcarbonyl, alkyl-S(O)$_n$ or haloalkyl-S(O)$_n$ in which n is 0, 1 or 2; and wherein the alkyl and alkoxy moieties are linear or branched chains of 1-4 carbon atoms and the halo substitution consists of one or more halogen atoms, which are the same or different, up to full substitution of the alkyl and alkoxy moieties; and X is a nitrogen atom (N) or C-$R^{14}$ in which $R^{14}$ is hydrogen, halogen, cyano, nitro, $C_{1-4}$ alkyl, $C_{1-4}$ alkylthio or $C_{1-4}$ alkoxy; and the alkyl moieties are linear or branched chains.

In the compounds of formula (I), defined above, when $R^4$ is heteroaryl it is preferably, but not limited to unsubstituted or substituted pyridyl, pyridyl N-oxide, thienyl, furanyl, pyrrolyl, imidazolyl, triazolyl or the like.

More preferred compounds of formula (I) are compounds, wherein:

$R^1$ is cyano, nitro or halogen;

$R^2$ is unsubstituted or substituted $R^9S(O)_n$, in which n is 0, 1 or 2 and $R^9$ is alkyl or haloalkyl as defined;

$R^3$ is hydrogen;

$R^4$ is unsubstituted or substituted phenyl or unsubstituted or substituted heteroaryl which is pyridyl, pyridyl N-oxide, thienyl, furanyl, pyrrolyl, imidazolyl or triazolyl;

$R^5$ is hydrogen, halogen or alkyl;

$R^6$ and $R^8$ are each individually hydrogen or fluorine;

$R^7$ is halogen, alkyl, haloalkyl or haloalkoxy; and

X is a nitrogen atom (N) or C-$R^{14}$ in which $R^{14}$ is hyrogen, halogen, cyano, alkyl, alkylthio or alkoxy.

Particularly preferred compounds of formula (I) are those compounds of a formula (Ia)

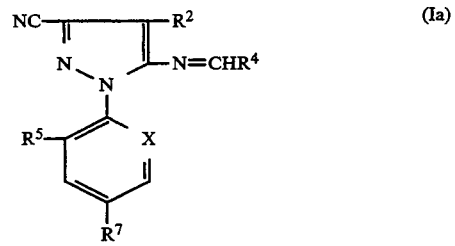

wherein:

$R^2$ is $R^9S(O)_n$ in which n is 0, 1 or 2 and $R^9$ is alkyl, preferably methyl; or haloalkyl, preferably trihalomethyl or dihalomethyl; and in which halo is F, Cl or Br or combinations thereof and most preferably $CF_3$, $CCl_3$, $CF_2Cl$, $CFCl_2$, $CF_2Br$, $CHF_2$, $CHClF$ or $CHCl_2$;

$R^4$ is unsubstituted or substituted phenyl in which the substituents are one or more: hydroxy; halogen, preferably F, Cl or Br; alkoxy, preferably methoxy or ethoxy; alkylthio, preferably methylthio; cyano; or alkyl, preferably methyl or ethyl; or combinations thereof; or $R^4$ is 4-pyridyl or 4-pyridyl N-oxide, optionally substituted as described for phenyl;

$R^5$ is: hydrogen; alkyl, preferably methyl; or halogen, preferably F, Cl or Br;

$R^7$ is: halogen, preferably F, Cl or Br; alkyl, preferably methyl; haloalkyl, preferably trihalomethyl and more preferably trifluoromethyl; or haloalkoxy, preferably trihalomethoxy and more preferably trifluoromethoxy; and in which halo is F, Cl or Br or combinations thereof; and X is a nitrogen atom or C-$R^{14}$ in which $R^{14}$ is: hydrogen; halogen, preferably F, Cl or Br; cyano; alkyl, preferably methyl or ethyl; alkylthio, preferably methylthio or ethylthio; or alkoxy, preferably methoxy or ethoxy.

For the above preferred compounds of formula (I), and particularly for (Ia), there are optimum combinations of substituent groups which optimize and maximize pesticidal activity based upon an optimum combination of chemical, physical and biological properties for each given compound. In particular those groups which function to provide particularly enhanced or unexpected and surprising pesticidal activity, as herein described, are, for example, as follows:

In the case of $R^4$, preferred groups are, for example:
1. 4-hydroxy-3-methoxyphenyl;
2. 4- hydroxyphenyl;
3. 3-hydroxy-4-methoxyphenyl;
4. 3,5-dimethyl-4-hydroxyphenyl;
5. 3,5-dimethoxy-4-hydroxyphenyl;
6. 4-methylthiophenyl;
7. 2,4-dihydroxyphenyl;
8. 4-hydroxy-3-methylphenyl;
9. 3-ethoxy-4-hydroxyphenyl;
10. 3,4,5-trimethoxyphenyl;
11. phenyl;
12. 2-hydroxyphenyl;
13. 3,4-dihydroxyphenyl;
14. 2,4-dimethylphenyl;
15. 4-cyanophenyl;
16. 4-pyridyl;
17. 4-pyridyl N-oxide;
18. 3-chloro-4-hydroxyphenyl;
19. 2-chloro-4-hydroxyphenyl;
20. 5-bromo-4-hydroxy-3-methoxyphenyl;
21. 3-hydroxyphenyl;

22. 5-chloro-4-hydroxy-3-methoxyphenyl;
23. 2,4,5-trihydroxyphenyl;
24. 5-bromo-3,4-dihydroxyphenyl; or
25. 4,5-dihydroxy-3-methoxyphenyl.

Of the above $R^4$ groups, even more preferred are individually group No's:
A) 1–10, 12–15, or 18–25; or
B) 1–5, 7–9, 13, or 18–25; or
C) 1–4, 18 or 19.

In the case of the 1-phenyl or 1-(2-pyridyl) group comprising the substituents $R^5$, $R^6$, $R^7$, $R^8$ and $R^{14}$, preferred groups are, for example:
1. 2,6-dichloro-4-trifluoromethylphenyl;
2. 2,6-dichloro-4-trifluoromethoxyphenyl;
3. 2-chloro-4-trifluoromethoxyphenyl;
4. 2-chloro-4-trifluoromethylphenyl;
5. 2,4,6-trichlorophenyl;
6. 2,6-dichloro-4-fluorophenyl;
7. 4-bromo-2,6-dichlorophenyl;
8. 2-chloro-6-methyl-4-trifluoromethylphenyl;
9. 2-chloro-6-methylthio-4-trifluoromethylphenyl;
10. 2,4-dichlorophenyl:
11. 2-chloro-4-fluorophenyl;
12. 2-chloro-4-bromophenyl;
13. 4-bromo-2,6-difluorophenyl;
14. 3-chloro-5-trifluoromethyl-2-pyridyl;
15. 3-chloro-5-trifluoromethoxy-2-pyridyl;
16. 3-chloro-5-fluoro-2-pyridyl;
17. 3,5-dichloro-2-pyridyl;
18. 2-bromo-4-trifluoromethoxyphenyl;
19. 2-bromo-4-trifluoromethylphenyl;
20. 2-chloro-6-fluoro-4-trifluoromethoxyphenyl;
21. 2-chloro-6-fluoro-4-trifluoromethylphenyl; or
22. 2-chloro-6-cyano-4-trifluoromethylphenyl.

Of these 1-phenyl or 1-(2-pyridyl) groups, even more preferred are group No's 1, 2, 3, 4, 5, 6, 7, 8, 14, 15, 16, 17, 18, 19, 20, 21 or 22. Even further preferred are group No's 1, 2, 3, 4, 5, 7, 8, 14, 21 or 22.

Among these compounds of formula (I) and more preferably (Ia) are the following preferred compounds, which provide particularly excellent control of larval insect species by ingestion or contact:

| CMPD NO. | |
|---|---|
| 2 | 1-(2,6-dichloro-4-trifluoromethylphenyl)-3-cyano-4-trifluoromethylsulfenyl-5-[(4-hydroxy-3-methoxyphenyl)methylideneimino]pyrazole; |
| 3 | 1-(2,6-dichloro-4-trifluoromethylphenyl)-3-cyano-4-trifluoromethylsulfonyl-5-[(4-hydroxy-3-methoxyphenyl)methylideneimino]pyrazole; |
| 4 | 1-(2,6-dichloro-4-trifluoromethylphenyl)-3-cyano-4-trifluoromethylsulfenyl-5-[(4-hydroxyphenyl)-methylideneimino]pyrazole; |
| 6 | 1-(2,6-dichloro-4-trifluoromethoxyphenyl)-3-cyano-4-dichlorofluoromethylsulfenyl-5-[(4-hydroxy-3-methoxyphenyl)methylideneimino]pyrazole; |
| 9 | 1-(2,6-dichloro-4-trifluoromethylphenyl)-3-cyano-4-dichlorofluoromethylsulfenyl-5-[(4-hydroxy-3-methoxyphenyl)methylideneimino]pyrazole; |
| 10 | 1-(2,6-dichloro-4-trifluoromethylphenyl)-3-cyano-4-trifluoromethylsulfinyl-5-[(4-hydroxy-3-methoxyphenyl)methylideneimino]pyrazole; |
| 13 | 1-(2,6-dichloro-4-trifluoromethylphenyl)-3-cyano-4-trifluoromethylsulfenyl-5-[(3,5-dimethoxy-4-hydroxyphenyl)methylideneimino]pyrazole; |
| 15 | 1-(2,6-dichloro-4-trifluoromethylphenyl)-3-cyano-4-trifluoromethylsulfenyl-5-[(3-hydroxy-4-methoxyphenyl)methylideneimino]pyrazole; |
| 16 | 1-(2,6-dichloro-4-trifluoromethylphenyl)-3-cyano-4-trifluoromethylsulfenyl-5-[(4-pyridyl)-methylideneimino]pyrazole; |
| 17 | 1-(2,6-dichloro-4-trifluoromethylphenyl)-3-cyano-4-trifluoromethylsulfenyl-5-[(2,4-dihydroxyphenyl)-methylideneimino]pyrazole; |
| 18 | 1-(2,6-dichloro-4-trifluoromethylphenyl)-3-cyano-4-trifluoromethylsulfenyl-5-[(4-pyridyl-N-oxide)methylideneimino]pyrazole; |
| 19 | 1-(2,6-dichloro-4-trifluoromethylphenyl)-3-cyano-4-trifluoromethylsulfenyl-5-[(4-hydroxy-3-methylphenyl)methylideneimino]pyrazole; |
| 22 | 1-(2,6-dichloro-4-trifluoromethylphenyl)-3-cyano-4-trifluoromethylsulfenyl-5-[(4-methylthiophenyl)-methylideneimino]pyrazole; |
| 23 | 1-(2,6-dichloro-4-trifluoromethylphenyl)-3-cyano-4-trifluoromethylsulfinyl-5-[(4-hydroxy-3-methylphenyl)methylideneimino]pyrazole; |
| 24 | 1-(2,6-dichloro-4-trifluoromethylphenyl)-3-cyano-4-trifluoromethylsulfenyl-5-[(3,5-dimethyl-4-hydroxyphenyl)methylideneimino]pyrazole; |
| 26 | 1-(2,6-dichloro-4-trifluoromethylphenyl)-3-cyano-4-trifluoromethylsulfinyl-5-[(3,5-dimethoxy-4-hydroxyphenyl)methylideneimino]pyrazole; |
| 29 | 1-(2,6-dichloro-4-trifluoromethylphenyl)-3-cyano-4-trifluoromethylsulfenyl-5-[(3-ethoxy-4-hydroxyphenyl)methylideneimino]pyrazole; |
| 30 | 1-(2,6-dichloro-4-trifluoromethylphenyl)-3-cyano-4-trifluoromethylsulfenyl-5-[(3,4,5-trimethoxyphenyl)-methylideneimino]pyrazole; |
| 37 | 1-(2,6-dichloro-4-trifluoromethylphenyl)-3-cyano-4-trifluoromethylsulfenyl-5-[(2-chloro-4-hydroxyphenyl)methylideneimino]pyrazole; |
| 38 | 1-(2,6-dichloro-4-trifluoromethylphenyl)-3-cyano-4-trifluoromethylsulfenyl-5-[(3-chloro-4-hydroxyphenyl)methylideneimino]pyrazole; or |
| 76 | 1-(2,6-dichloro-4-trifluoromethoxyphenyl)-3-cyano-4-dichlorofluoromethylsulfenyl-5-[(4-hydroxy-phenyl)-methylideneimino]pyrazole. |

Of these specific named compounds, there are more preferred CMPD No's 2, 3, 4, 6, 9, 10, 13, 15, 17, 19, 23, 24, 26, 29, 37, 38 or 76 and especially preferred CMPD No's 2, 3, 10, 15, 24, 37, 38 or 76.

There are additionally other more specific categories of compounds that are specially preferred compounds of formula (I) or (Ia), which are compounds of the invention, wherein the $R^4$ group is a phenyl radical, which is at least substituted by 3-hydroxy or 4-hydroxy and the other phenyl radical substituents are as described by any of the independent definitions of the invention. These 3-hydroxy or 4-hydroxy compounds thus form separate and distinct subclasses independently within each of the above already indicated preferences and additional preferences, indicated as follows, which are further meant to be independent from each other. Furthermore, individual $R^4$ moieties, individual 1-phenyl or 1-(2-pyridyl) moieties, or individual compounds (CMPD No), within preferences C-L below, are each individually hereby meant to be separate independent preferences of the invention.

A) Compounds of formula (I);
B) Compounds of formula (Ia):
C) Preferred $R^4$ groups 1–25;
D) Preferred $R^4$ groups 1–10, 12–15 or 18–25;
E) Preferred $R^4$ groups 1–5, 7–9, 13 or 18–25;
F) Preferred $R^4$ groups 1–4, 18 or 19;
G) 1-Phenyl or 1-(2-pyridyl) groups 1–22;
H) 1-Phenyl or 1-(2-pyridyl) groups 1–8 or 14–22;
I) 1-Phenyl or 1-(2-pyridyl) groups 1–5, 7, 8, 14, 21 or 22:
J) CMPD No's 2, 3, 4, 6, 9, 10, 13, 15, 16, 17, 18, 19, 22, 23, 24, 26, 29, 30, 37, 38 or 76;
K) CMPD No's 2, 3, 4, 6, 9, 10, 13, 15, 17, 19, 23, 24, 26, 29, 37, 38 or 76; or L) CMPD No's 2, 3, 10, 15, 24, 37, 38 or 76.

It is an object of the present invention to provide pesticidal new compounds of the 1-aryl-5-(substituted alkylideneimino)pyrazole family together with processes for their preparation.

A second object of the present invention is to provide compounds with a rather simple chemical formula that are readily prepared from known and/or readily available and frequently inexpensive intermediates and starting materials.

A third object of the present invention is to provide pesticidal compositions and pesticidal methods of use of the pesticidal pyrazole compounds against arthropods, especially insects, plant nematodes, or helminth or protozoan pests, particularly in agricultural or horticultural crops, forestry, veterinary medicine or livestock husbandry, or in public health.

A forth object of the present invention is to provide very active compounds, with broad spectrum pesticidal activity, as well as compounds with selective special activity, e.g., aphicidal, miticidal, foliar insecticidal, soil insecticidal and nematicidal, systemic, antifeeding, or pesticidal activity via seed treatment.

A fifth object of the present invention is to provide compounds with substantially enhanced and more rapid activity, especially against insects and more particularly insects in their larval stages, especially by contact action.

A sixth object of the present invention is to provide compounds with greatly improved (greater and faster) penetration into pest species when topically applied and thus provide enhanced movement of the compounds to the pesticidal site(s) of action within the pest.

Another object of the present invention is to provide compounds with high activity and improved safety to the user and the environment, which are obtained by optimization of chemical, physical and biological properties such as solubility, melting point, stability, electronic and steric parameters, and the like.

These and other objects of the invention shall become readily apparent from the detailed description of the present invention.

DESCRIPTION OF THE PREFERRED EMBODIMENTS

Methods or Processes of Synthesis

The compounds of general formula (I) can be prepared by the application or adaptation of known methods (i.e. methods heretofore used or described in the chemical literature): e.g. an intermediate 5-aminopyrazole compound of a formula (II), initially prepared by known procedures, is subsequently condensed by well-known methods 1) with an appropriately substituted aldehyde or ketone to give compounds wherein $R^3$ is hydrogen or alkyl, respectively, or 2) with an orthoester to give compounds wherein $R^3$ is alkoxy, which optionally are reacted with an alkylthiol or dialkylamine, in the presence of a base such as NaH, $K_2CO_3$ and $Na_2CO_3$, to give compounds wherein $R^3$ is alkylthio or dialkylamino.

The intermediate 5-amino-1-phenylpyrazole intermediates of formula (II) are known or can be prepared by methods or processes as described in EP 295, 117, published Dec. 14, 1988; EP 295, 118, published Dec. 14, 1988; EP 234,119, published Sep. 2, 1987 (also corresponding to WO 87/03781, published Jul. 2, 1987); and EP 350,311, published Jan. 10, 1990; all of which are incorporated herein by reference.

In an analogous manner for the preparation of the 5-amino-1-phenylpyrazole intermediates, the 5-amino-1-(2-pyridyl)pyrazole intermediates can be prepared by a variety of similar methods. According to a preferred synthetic method, these compounds can be obtained from an intermediate 1-(substituted-2-pyridyl)-3-alkoxycarbonyl-5-aminopyrazole compound followed by further substitution or derivatization using analogous procedures to these described for the 5-amino-1-phenylpyrazole compounds. The 5-amino-1-(2-pyridyl)-pyrazole intermediate is initially obtained by cyclizing, in the presence of a base, an alkyl 2-oxo-3-cyanopropionate, obtained by acid neutralization of its corresponding metal enolate salt, with an appropriately substituted 2-pyridylhydrazine. The hydrazine is either commercially available or is generally a known compound of organic chemistry, prepared by known literature procedures familiar to one skilled in the art.

The aldehydes, ketones, ortho esters, alkylthiols and dialkylamines are also generally known compounds of organic chemistry and usually commercially available or can be prepared from such available compounds by known methods.

The compounds of formula (I), chemically described as Schiff bases, are prepared in a condensation reaction, for example, of an aldehyde or ketone of formula (III) with an aminopyrazole of formula (II), according to the following reaction:

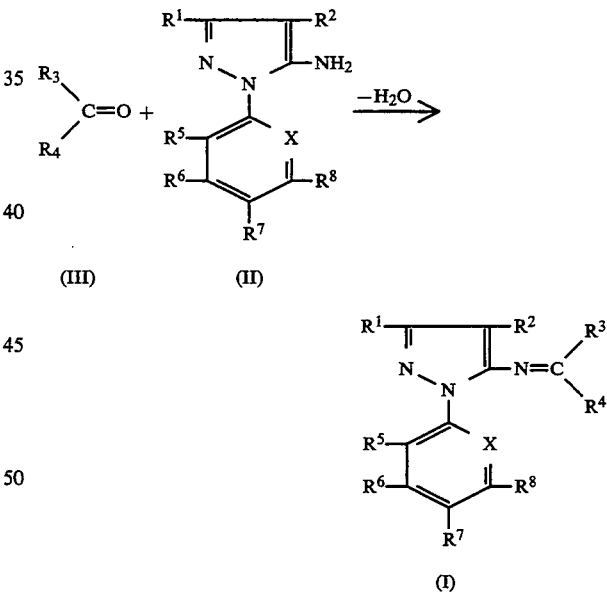

wherein the substituents $R^1$ through $R^8$ are as hereinabove defined.

In the reaction shown above, the aldehyde or ketone is optionally replaced by the above described ortho ester, $R^4C(O-C_{1-4}$ alkyl$)_3$, and removal of the formed alcohol, to provide compounds wherein $R^3$ is alkoxy, which is optionally converted to $R^3$ is alkylthio or dialkylamino.

The proper conditions for formation of the Schiff base will depend upon the nature of the starting materials and the product formed, that is to say solubility, reactivity, stability, etc. While such conditions may be required to be individually selected, in general, the compounds of formula (I) can readily be prepared by known condensation methods such as those described by J. March in "Advanced Organic Chemistry", McGraw-Hill, publ. (1985), p. 1165 and references cited therein.

pounds within the purview of the above general formula (I) and can be prepared by the herein described methods or processes of synthesis, by the appropriate selection of reactants, conditions and procedures, which are commonly known and apparent to one skilled in the art.

REPRESENTATIVE COMPOUNDS OF THE INVENTION

The compounds of TABLE 1 are illustrative of some of the preferred compounds or subgroups of compounds

TABLE 1

REPRESENTATIVE 1-ARYL-5-(SUBSTITUTED ALKYLIDENEIMINO)PYRAZOLES OF FORMULA (I): (Ph = PHENYL)

| NO. | $R^1$ | $R^2$ | $R^3$ | $R^4$ |
|---|---|---|---|---|
| A) Wherein: $R^5$ = Cl, $R^6$ & $R^8$ = H, $R^7$ = $CF_3$, and X = CCl | | | | |
| A-1) | | | | |
| 1 | CN | $SCF_3$ | $CH_3$ | 4-OH—Ph |
| 2 | CN | $SCF_3$ | H | 2-pyrrolyl |
| 3 | CN | $SCF_3$ | H | N—$CH_3$-2-pyrrolyl |
| 4 | CN | $SCCl_2F$ | H | 3,4-$(OH)_2$—Ph |
| 5 | CN | $SCCl_2F$ | H | 4-OH—Ph |
| 6 | CN | $SCCl_2F$ | H | 3-OH-4-$OCH_3$—Ph |
| 7 | CN | $SCCl_2F$ | H | 2,4-$(OH)_2$—Ph |
| 8 | CN | $SCCl_2F$ | H | 3,5-$(OCH_3)_2$-4-OH—Ph |
| 9 | CN | $SCClF_2$ | H | 4-OH-3-$OCH_3$—Ph |
| 10 | CN | $SCClF_2$ | H | 3,5-$(CH_3)_2$-4-OH—Ph |
| A-2) | | | | |
| 11 | Cl | $SCF_3$ | H | 4-OH-3-$OCH_3$—Ph |
| 12 | Cl | $SO_2CF_3$ | H | 4-OH—Ph |
| 13 | Cl | $SCCl_2F$ | H | 3-OH—Ph |
| 14 | Cl | $SCCl_2F$ | H | 4-OH-3-$OCH_3$—Ph |
| 15 | Br | $SCF_3$ | H | 3,5-$(CH_3)_2$-4-OH—Ph |
| A-3) | | | | |
| 16 | Br | $NO_2$ | H | 4-OH-3-$OCH_3$—Ph |
| 17 | Br | $NO_2$ | H | 3,5-$(CH_3)_2$-4-OH—Ph |
| 18 | Br | $NO_2$ | H | 3,5-$(OCH_3)_2$-4-OH—Ph |
| 19 | Br | $NO_2$ | H | 3-OH-4-$OCH_3$—Ph |
| B) Wherein: $R^5$ = Cl, $R^6$ & $R^8$ = H, $R^7$ = $CF_3$, and X = CF | | | | |
| 20 | CN | $SCF_3$ | H | 4-OH-3-$OCH_3$—Ph |
| 21 | CN | $SCF_3$ | H | 3,5-$(CH_3)_2$-4-OH—Ph |
| 22 | CN | $SCF_3$ | H | 4-OH-3-$CH_3$—Ph |
| 23 | CN | $SCF_3$ | H | 4-OH—Ph |
| 24 | CN | $SCF_3$ | H | 3,5-$(OCH_3)_2$-4-OH—Ph |
| 25 | CN | $SCCl_2F$ | H | 4-OH-3-$OCH_3$—Ph |
| 26 | CN | $SCClF_2$ | H | 4-OH-3-$OCH_3$—Ph |
| C) Wherein: $R^5$ = Cl, $R^6$ & $R^8$ = H, $R^7$ = $OCF_3$, and X = CCl | | | | |
| 27 | CN | $SCF_3$ | H | 4-OH-3-$OCH_3$—Ph |
| 28 | CN | $SCF_3$ | H | 4-OH—Ph |
| 29 | CN | $SCF_3$ | H | 3-OH-4-$OCH_3$—Ph |
| 30 | CN | $SCF_3$ | H | 3,5-$(CH_3)_2$-4-OH—Ph |
| 31 | CN | $SCF_3$ | H | 3-OH—Ph |
| 32 | CN | $SOCF_3$ | H | 4-OH-3-$CH_3$—Ph |
| 33 | CN | $SOCF_3$ | H | 3,5-$(CH_3)_2$-4-OH—Ph |
| 34 | CN | $SO_2CF_3$ | H | 4-OH-3-$OCH_3$—Ph |
| 35 | CN | $SCCl_2F$ | H | 3,4-$(OH)_2$—Ph |
| 36 | CN | $SCCl_2F$ | H | 4-OH—Ph |
| 37 | CN | $SCCl_2F$ | H | 3-OH-4-$OCH_3$—Ph |
| 38 | CN | $SCCl_2F$ | H | 2,4-$(OH)_2$—Ph |
| 39 | CN | $SCCl_2F$ | H | 4-pyridyl N—O |
| D) Wherein: $R^5$, $R^6$ & $R^8$ = H, $R^7$ = $CF_3$, and X = CBr or CCl | | | | |
| 40 | CN | $SCF_3$ | H | 4-OH-3-$OCH_3$—Ph |
| 41 | CN | $SCF_3$ | H | 3,5-$(CH_3)_2$-4-OH—Ph |
| 42 | CN | $SCF_3$ | H | 4-OH—Ph |
| 43 | CN | $SCF_3$ | H | 3-OH-4-$OCH_3$—Ph |
| 44 | CN | $SCF_3$ | H | 4-OH-3-$CH_3$—Ph |
| 45 | CN | $SO_2CF_3$ | H | 4-OH-3-$CH_3$—Ph |
| 46 | CN | $SCCl_2F$ | H | 3,5-$(CH_3)_2$-4-OH—Ph |
| 47 | CN | $SCCl_2F$ | H | 4-OH—Ph |
| 48 | CN | $SCCl_2F$ | H | 3,5-$(OCH_3)_2$-4-OH—Ph |
| 49 | CN | $SCCl_2F$ | H | 3-OH-4-$OCH_3$—Ph |
| 50 | CN | $SCClF_2$ | H | 4-OH-3-$OCH_3$—Ph |
| E) Wherein: $R^5$, $R^6$ & $R^8$ = H, $R^7$ = $OCF_3$, and X = CBr or CCl | | | | |
| 51 | CN | $SCF_3$ | H | 4-OH-3-$OCH_3$—Ph |
| 52 | CN | $SOCF_3$ | H | 4-OH-3-$OCH_3$—Ph |
| 53 | CN | $SOCF_3$ | H | 4-OH-3-$CH_3$—Ph |
| 54 | CN | $SO_2CF_3$ | H | 4-OH-3-$CH_3$—Ph |
| 55 | CN | $SCF_3$ | H | 3,5-$(CH_3)_2$-4-OH—Ph |
| 56 | CN | $SCF_3$ | H | 3-OH-4-$OCH_3$—Ph |
| 57 | CN | $SCF_3$ | H | 4-OH—Ph |

TABLE 1-continued

REPRESENTATIVE 1-ARYL-5-(SUBSTITUTED ALKYLIDENEIMINO)PYRAZOLES OF FORMULA (I): (Ph = PHENYL)

| NO. | $R^1$ | $R^2$ | $R^3$ | $R^4$ |
|---|---|---|---|---|
| 58 | CN | $SCCl_2F$ | H | $3,5-(CH_3)_2-4-OH-Ph$ |
| 59 | CN | $SCCl_2F$ | H | $4-OH-Ph$ |
| 60 | CN | $SCCl_2F$ | H | $3,5-(OCH_3)_2-4-OH-Ph$ |
| 61 | CN | $SCCl_2F$ | H | $3-OH-4-OCH_3-Ph$ |
| 62 | CN | $SCClF_2$ | H | $4-OH-3-OCH_3-Ph$ |
| F) Wherein: $R^5$ = Cl, $R^6$ & $R^8$ = H, $R^7$ = Br, and X = CCl | | | | |
| 63 | CN | $SOCF_3$ | H | $4-OH-3-OCH_3-Ph$ |
| 64 | CN | $SO_2CF_3$ | H | $4-OH-3-OCH_3-Ph$ |
| 65 | CN | $SCCl_2F$ | H | $3,4-(OH)_2-Ph$ |
| 66 | CN | $SCF_3$ | H | 4-pyridyl N—O |
| 67 | CN | $SCF_3$ | H | $3-OH-4-OCH_3-Ph$ |
| 68 | CN | $SCF_3$ | H | $3,5-(CH_3)_2-4-OH-Ph$ |
| 69 | CN | $SCF_3$ | H | $4-OH-Ph$ |
| 70 | CN | $SCF_3$ | H | $3,5-(OCH_3)_2-4-OH-Ph$ |
| G) Wherein: $R^5$ = Cl, $R^6$ & $R^8$ = H, $R^7$ = Cl, and X = CCl | | | | |
| 71 | CN | $SCCl_2F$ | H | $4-OH-Ph$ |
| 72 | CN | $SCCl_2F$ | H | $4-OH-3-OCH_3-Ph$ |
| 73 | CN | $SCF_3$ | H | $4-OH-3-CH_3-Ph$ |
| 74 | CN | $SCF_3$ | H | $4-OH-3-OCH_3-Ph$ |
| H) Wherein: $R^5$ = Cl, $R^6$ & $R^8$ = H, $R^7$ = F, and X = CCl | | | | |
| 75 | CN | $SCCl_2F$ | H | $4-OH-3-OCH_3-Ph$ |
| 76 | CN | $SCF_3$ | H | $4-OH-Ph$ |
| 77 | CN | $SCF_3$ | H | $4-OH-3-OCH_3-Ph$ |
| I) Wherein: $R^5$ = Cl, $R^6$ & $R^8$ = H, $R^7$ = $CF_3$, and X = N | | | | |
| 78 | CN | $SCF_3$ | H | $3,5-(CH_3O)_2-4-OH-Ph$ |
| 79 | CN | $SCCl_2F$ | H | $4-OH-3-OCH_3-Ph$ |
| 80 | CN | $SCF_3$ | H | $4-OH-3-OCH_3-Ph$ |
| 81 | CN | $SOCF_3$ | H | $4-OH-3-OCH_3-Ph$ |
| 82 | CN | $SO_2CF_3$ | H | $4-OH-3-OCH_3-Ph$ |
| 83 | CN | $SCCl_2F$ | H | $3-OH-4-OCH_3-Ph$ |
| 84 | CN | $SCCl_2F$ | H | $4-OH-Ph$ |
| 85 | CN | $SCF_3$ | H | $3,5-(OCH_3)_2-4-OH-Ph$ |
| J) Wherein: $R^5$ = Cl, $R^6$ & $R^8$ = H, $R^7$ = $CF_3$, $OCF_3$, Br or Cl, and X = CCl | | | | |
| 86 | Cl | Cl | $CH_3$ | $4-Cl-Ph$ |
| 87 | CHO | $CH_3$ | H | $4-CN-Ph$ |
| 88 | $CH_3CO$ | $NO_2$ | H | $4-NO_2-Ph$ |
| 89 | 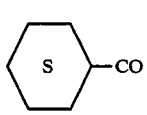 | $OCH_3$ | H | $4-OH-Ph$ |
| 90 | CN | $CF_3$ | $CH_3$ | $4-OH-3-OCH_3-Ph$ |
| 91 | CN | $OCF_3$ | H | $2,4-(OH)_2-Ph$ |
| 92 | $NO_2$ | $CH_3$ | $CH_3$ | $3,4-(OH)_2-Ph$ |
| 93 | Br | SCN | H | $3-OH-Ph$ |
| 94 | CN | $SO_2NH_2$ | H | $4-OH-3-OCH_3-Ph$ |
| 95 | Cl | $CONHCH_3$ | H | $2-OH-Ph$ |
| 96 | $NO_2$ | $COOCH_3$ | $CH_3$ | $2,4-(CH_3)_2-Ph$ |
| 97 | CN | $SO_2CH_3$ | H | $3-OH-4-OCH_3-Ph$ |
| 98 | CN | $SCF_3$ | H | $4-CF_3-3-OH-Ph$ |
| 99 | Cl | $SOCF_3$ | $CH_3$ | $3-OCF_3-Ph$ |
| 100 | CN | $NO_2$ | H | $4-O_2CCH_3-Ph$ |
| 101 | $NO_2$ | Cl | $CH_3$ | $4-OPh-Ph$ |
| 102 | CN | $SCF_3$ | H | $4-Ph-Ph$ |
| 103 | CN | $SCCl_2F$ | H | $3-SO_2CH_3-Ph$ |
| 104 | CN | $SCF_3$ | H | $3-SCF_3-Ph$ |
| 105 | Br | $SCF_3$ | H | $4-N(CH_3)_2-Ph$ |
| 106 | Cl | $NO_2$ | $CH_3$ | $4-COOCH_3-Ph$ |
| 107 | CN | $SCF_3$ | H | $3-SO_3CH_3-Ph$ |
| 108 | CN | $SCF_3$ | $SCH_3$ | $4-OH-3-OCH_3-Ph$ |
| 109 | CN | $SOCF_3$ | $N(CH_3)_2$ | $4-OH-3-OCH_3-Ph$ |
| 110 | CN | $SCF_3$ | $OC_2H_5$ | $4-OH-Ph$ |
| 111 | CN | $SCF_3$ | H | $3-OCH_3-4-OSi(CH_3)_3-Ph$ |
| K) Wherein: $R^5$ = Cl, $R^6$ & $R^8$ = H, $R^7$ = $CH_3$, $OCH_3$, CN, $NO_2$, $COCH_3$, $COCF_3$, $SOCH_3$, $SO_2CH_3$, $SOCF_3$ or $SO_2CF_3$, and X = CCl | | | | |
| 112 | CN | $SCF_3$ | H | $4-OH-Ph$ |
| 113 | Cl | $NO_2$ | $CH_3$ | $3-OH-4-CH_3-Ph$ |
| 114 | CN | $SOCF_3$ | $SC_2H_5$ | $3-OH-Ph$ |
| 115 | CN | $SCF_3$ | $OC_4H_9$ | $2,4-(OH)_2-Ph$ |
| 116 | CN | Cl | $N(C_2H_5)_2$ | $4-OH-Ph$ |
| L) Wherein: $R^5$ = $CH_3$, $R^6$ & $R^8$ = F, $R^7$ = $CF_3$, and X = $CCH_3$, CH, CCN, $CNO_2$, $COCH_3$ or $CSCH_3$ | | | | |
| 117 | Cl | $NO_2$ | H | $4-OH-Ph$ |
| 118 | CN | $SCCl_2F$ | $CH_3$ | $3-OH-4-OCH_3-Ph$ |

TABLE 1-continued

REPRESENTATIVE 1-ARYL-5-(SUBSTITUTED ALKYLIDENEIMINO)PYRAZOLES OF FORMULA (I): (Ph = PHENYL)

| NO. | $R^1$ | $R^2$ | $R^3$ | $R^4$ |
|-----|-------|-------|-------|-------|
| 119 | CN | $SCF_3$ | H | 2,4-$(OH)_2$—Ph |

M) Wherein: $R^5$ = Cl or Br, $R^6$ & $R^8$ = H, $R^7$ = $CF_3$ or $OCF_3$, and X = CH, $CCH_3$, CCN, $CNO_2$, $COCH_3$ or $CSCH_3$

| NO. | $R^1$ | $R^2$ | $R^3$ | $R^4$ |
|-----|-------|-------|-------|-------|
| 120 | CN | $SCF_3$ | H | 4-OH-3-$OCH_3$—Ph |
| 121 | CN | $SCCl_2F$ | H | 4-OH-3-$OCH_3$—Ph |
| 122 | CN | $SCF_3$ | H | 4-OH—Ph |
| 123 | CN | $SO_2CF_3$ | H | 4-OH-3-$CH_3$—Ph |

DETAILED EXAMPLES OF COMPOUND SYNTHESIS

The following EXAMPLES 1 to 5 illustrate detailed methods of synthesis and the physical properties of representative pesticidal compounds of formula (I) (and their chemical intermediates) according to the invention. These example compounds and others prepared in a similar manner, following the detailed procedures or other methods or processes herein described, are shown in Tables 2, 2A and 2B. Reported melting points for the compounds in these EXAMPLES, as well as those in Tables 2, 2A and 2B, represent the average value of an observed melting point range determined for a compound or furthermore represent the average value of a number of separate melting point determinations. Additionally, one or more spectroscopic analyses (IR, $H^1$ or $F^{19}$ NMR, MS, etc.) have been performed on each compound for characterization and confirmation of the chemical structure.

The condensation is preferably carried out in the presence of a suitable reaction auxiliary. Those auxiliaries which are suitable are: organic or inorganic acids, for example, sulfuric acid, hydrochloric acid, phosphoric acid, toluenesulfonic acid or methanesulfonic acid; ion exchange resin catalysts; and/or water-removing agents, for example, sodium (or magnesium) sulfate or molecular sieves. It is also possible to optionally remove reaction water from the reaction mixture by azotropic distillation to facilitate the reaction.

Particularly preferred reaction auxiliaries are ion exchange resins of the commercial type sold by Dow Chemical Company under the trademark "DOWEX ®" or by Bio-Rad Chemical Division under the trademark "AG ®", "BIO-REX ®" or "CHELEX ®". These latter Bio-Rad resins, their properties and uses are extensively described in "Bio-Rad Guide to Ion Exchange" catalog Number 140-997 (and references described therein), Bio-Rad Chemical Division, 1414 Harbour Way South, Richmond, Calif. 94804. The resins of this type are also described in "The Chemist's Companion", Gorden, A. J. and Ford, R. A., page 386, John Wiley and Sons.

Particularly preferred are acidic cationic exchange resins, for example, as follows:

| | |
|---|---|
| 1. Strong sulfonic acid ($RCH_2SO_3H$) phenolic type resin | "BIO-REX ®" 40 |
| 2. Strong sulfonic acid ($\phi SO_3H$) polystyrene type resin | "AGO ®" 50W (X Series) ("DOWEX ®" 50 (X Series) |
| 3. Intermediate phosphonic acid ($\phi PO_3Na$) polystyrene type resin | "BIO-REX ®" 63 |
| 4. Weak Acid (RCOONa) acrylic type resin | "BIO-REX ®" 70 |
| 5. Weak Acid Chelating ($\phi CH_2N(CH_2COOH)_2$) polystyrene type resin | "CHELEX ®" 100 |

These commercial resins maybe in protonic acid form or as salts. In the event they are salts, it may be necessary to appropriately convert them to a proper acid form for best catalysis of the condensation reaction.

The use of these ion exchange resin catalysts is especially advantageous or beneficial since:

a) they can be readily removed, for example, by simple filtration;

b) they avoid aqueous basic washes of the reaction product when typical organic or inorganic acid catalysts are used;

c) they avoid hydrolysis of the desired product;

d) they are more efficient/effective in providing higher yields, higher purities and faster reaction rates;

e) they are available in very small to large particle sizes which allows better reaction results/control;

f) they provide more precise catalytic acidity range and control;

g) they are more reproducible in their results;

h) they are more economical since they can be used, then reused/recycled numerous times; and i) they are more flexible in their use in batch, semi-continuous or continuous reaction processes.

The reaction temperatures for the condensation reaction can be varied within a relatively wide range. In general, the reaction is carried out at temperatures between about 70° C. and about 160° C., preferably at temperatures between about 100° C. and about 130° C.

For carrying out the process according to the invention, 1.0 to 5.0 equivalents, preferably 1.0 to 1.5 equivalents, of aldehyde or ketone of the formula (III) and 0.01 to 2.0 equivalents, preferably 0.01 to 0.5 equivalents, of the reaction auxiliary are generally employed. In the case of ionic resin catalysts as reaction auxiliaries, they may be used at lower as well as higher equivalencies. The reaction is carried out and the reaction products are worked up and isolated by generally customary methods.

Suitable diluents, which in some cases may be optional, for carrying out the process are inert, typically aprotic, organic solvents, which include aliphatic, alicyclic or aromatic, or optionally halogenated hydrocarbons, for example, benzene, chlorobenzene, toluene or xylene.

EXAMPLE 1

Preparation of:
1-(2,6-dichloro-4-trifluoromethylphenyl)-3-cyano-4-trifluoromethylsulfenyl-5-[(4-hydroxy-3-methoxyphenyl)-methylideneimino]pyrazole; CMPD No. 2

A mixture of 5-amino-1-(2,6-dichloro-4-trifluoromethylphenyl)-3-cyano-4-trifluoromethylsulfenylpyrazole (2.5 g, 5.9 mmol), 4-hydroxy-3-methoxybenzaldehyde (1.1 g, 1.3 equivalents), p-toluenesulfonic acid (0.15 g, 0.13 equivalents) and toluene (750 mL) was heated at reflux with a Dean-Stark trap to remove water for 40 hours. Toluene was removed in vacuo. The residue was dissolved with ethyl acetate. The organic solution was washed once with saturated aqueous $Na_2CO_3$, then water, dried over $MgSO_4$, filtered and concentrated in vacuo. The desired product (2.8 g. 85% of theory) was obtained as a light yellow solid, mp 132.5° C. $H^1$ and $F^{19}$ NMR spectral data indicated it to be pure.

EXAMPLE 2

Preparation of:
1-(2.6-dichloro-4-trifluoromethylphenyl)-3-cyano-4-trifluoromethylsulfenyl-5-[(4-nitrophenyl)methylideneimino]pyrazole; CMPD No. 33

A mixture of 5-amino-1-(2,6-dichloro-4-trifluoromethylphenyl)-3-cyano-4-trifluoromethylsulfenylpyrazole (2.0 g, 4.7 mmol), 4-nitrobenzaldehyde (0.87 g, 1.25 equivalents), p-toluenesulfonic acid (0.02 g, 0.02 equivalents) and toluene (200 mL) was heated at reflux with a Dean-Stark trap to remove water for 36 hours. After cooling to room temperature, the toluene solution was agitated with aqueous $NaHSO_3$ solution in an ice bath for five minutes. Two phases were separated. This was repeated one more time. The organic layer was then washed with water, dried over $MgSO_4$, filtered and concentrated in vacuo. The crude product was recrystallized from t-butyl methyl ether and hexane to give the desired product (1.42 g,. 54.4% yield) as a yellow solid, mp 167.5° C.

EXAMPLE 3

Preparation of:
1-(2,6-dichloro-4-trifluoromethylphenyl)-3-cyano-4-trifluoromethylsulfinyl-5-[(3,5-dimethoxy-4-hydroxyphenyl)methylideneimino]pyrazole; CMPD No. 26

A mixture of 5-amino-1-(2,6-dichloro-4-trifluoromethylphenyl)-3-cyano-4-trifluoromethylsulfinylpyrazole (2.0 g, 4.58 mmol), 3,5-dimethoxy-4-hydroxybenzaldehyde (1.0 g. 1.2 equivalents), p-toluenesulfonic acid (0.08 g, 0.1 equivalents) and toluene (800 mL) was heated at reflux with a Dean-Stark trap to remove water for eight days. The reaction solution was concentrated to 100 mL in vacuo and ethyl acetate was added. The organic solution was washed with saturated aqueous $Na_2CO_3$, dried over $MgSO_4$, filtered and concentrated in vacuo. The residue was purified by silica gel column chromatography, eluted with hexane/ethyl acetate. The desired product (1.2 g) as a yellow solid (yield: 44%), was obtained, mp. 175° C.

EXAMPLE 4

Preparation of:
1-(2.6-dichloro-4-trifluoromethylphenyl)-3-cyano-4-trifluoromethylsulfinyl-5-[(3-methoxy-4-hydroxyphenyl)-methylideneimino]pyrazole: CMPD. No. 10

A mixture of 5-amino-1-(2,6-dichloro-4-trifluoromethylphenyl)-3-cyano-4-trifluoromethylsulfinylpyrazole (60 g, 0.137 mole), 3-methoxy-4-hydroxybenzaldehyde (25.6 g, 1.2 equivalents), "DOWEX®" (trademark) 50×8-400 resin (140 g) and toluene (1.5 L) was heated at reflux with a Dean-Stark tube to remove water for four days. After cooling to room temperature, the reaction mixture was filtered. The toluene filtrate was concentrated in vacuo. The solid residue was ground, and then heated at reflux with heptane (600 mL). A yellow solid was filtered while the mixture was still hot. The solid (66.5 g) was obtained as the desired product, m.p. 155° C.

EXAMPLE 5

Preparation of:
1-(2,6-dichloro-4-trifluoromethylphenyl)-3-cyano-4-trifluoromethylsulfenyl-5-[(3-methoxy-4-hydroxyphenyl)-methylideneimino]pyrazole: CMPD. No. 2

A mixture of 5-amino-1-(2,6-dichloro-4-trifluoromethylphenyl)-3-cyano-4-trifluoromethylsulfenylpyrazo (5 g, 11.8 mmol), 3-methoxy-4-hydroxybenzaldehyde (2 g, 1.1 equivalents), "DOWEX®" (trademark) 50×8-100 resins (2 g) and toluene (400 mL) was heated at reflux with a Dean-Stark tube for 30 hours. After cooling to room temperature, the mixture was filtered through a thin layer of silica gel and celite. The filtrate was concentrated and the desired product as a white solid was obtained (6.85 g), m.p. 132.5° C.

Using similar procedures to those of EXAMPLES 1 to 5, there were obtained the following other compounds as shown in TABLES 2, 2A, and 2B.

TABLE 2

SYNTHESIZED PYRAZOLE COMPOUNDS OF FORMULA (I), WHEREIN: $R^1$ IS CN AND $R^3$, $R^6$ AND $R^8$ ARE H (Ph = PHENYL)

| CMPD NO | $R^2$ | $R^5$ | $R^7$ | X | $R^4$ | M.P. °C. |
|---|---|---|---|---|---|---|
| 1 | $SCF_3$ | Cl | $CF_3$ | CCl | 2-OH—Ph | 158 |
| 2 | $SCF_3$ | Cl | $CF_3$ | CCl | 4-OH-3-$OCH_3$—Ph | 132.5 |
| 3 | $SO_2CF_3$ | Cl | $CF_3$ | CCl | 4-OH-3-$OCH_3$—Ph | 177 |
| 4 | $SCF_3$ | Cl | $CF_3$ | CCl | 4-OH—Ph | 139 |
| 5 | $SCF_3$ | Cl | $CF_3$ | CCl | 3-OPh—Ph | Oil |
| 6 | $SCCl_2F$ | Cl | $OCF_3$ | CCl | 4-OH-3-$OCH_3$—Ph | 172 |
| 7 | $SCF_3$ | Cl | $CF_3$ | CCl | 2-thienyl | 110 |
| 8 | $SCF_3$ | Cl | Br | CCl | 4-OH-3-$OCH_3$—Ph | Oil |
| 9 | $SCCl_2F$ | Cl | $CF_3$ | CCl | 4-OH-3-$OCH_3$—Ph | 69 |
| 10 | $SOCF_3$ | Cl | $CF_3$ | CCl | 4-OH-3-$OCH_3$—Ph | 155 |
| 11 | $SCF_3$ | Cl | $CF_3$ | CCl | 3,4-$(OH)_2$—Ph | 74 |
| 12 | $SCF_3$ | Cl | $CF_3$ | CCl | 3,4-$(OCH_2O)$—Ph | 140 |
| 13 | $SCF_3$ | Cl | $CF_3$ | CCl | 3,5-$(OCH_3)_2$-4-OH—Ph | 162.5 |
| 14 | $SCF_3$ | Cl | $CF_3$ | CCl | 4-$N(CH_3)_2$—Ph | 144.5 |
| 15 | $SCF_3$ | Cl | $CF_3$ | CCl | 3-OH-4-$OCH_3$—Ph | 162 |

TABLE 2-continued

SYNTHESIZED PYRAZOLE COMPOUNDS OF FORMULA (I), WHEREIN: $R^1$ IS CN AND $R^3$, $R^6$ AND $R^8$ ARE H (Ph = PHENYL)

| CMPD NO | $R^2$ | $R^5$ | $R^7$ | X | $R^4$ | M.P. °C. |
|---|---|---|---|---|---|---|
| 16 | $SCF_3$ | Cl | $CF_3$ | CCl | 4-pyridyl | 157 |
| 17 | $SCF_3$ | Cl | $CF_3$ | CCl | 2,4-$(OH)_2$—Ph | 162 |
| 18 | $SCF_3$ | Cl | $CF_3$ | CCl | 4-pyridyl N—O | 189 |
| 19 | $SCF_3$ | Cl | $CF_3$ | CCl | 4-OH-3-$CH_3$—Ph | 178.5 |
| 20 | $SCF_3$ | Cl | $CF_3$ | CCl | 2-furanyl | 169 |
| 21 | $SCF_3$ | Cl | $CF_3$ | CCl | 4-$OCH_3$—Ph | 95.5 |
| 22 | $SCF_3$ | Cl | $CF_3$ | CCl | 4-$SCH_3$—Ph | 113 |
| 23 | $SOCF_3$ | Cl | $CF_3$ | CCl | 4-OH-3-$CH_3$—Ph | 176 |
| 24 | $SCF_3$ | Cl | $CF_3$ | CCl | 3,5-$(CH_3)_2$-4-OH—Ph | 183 |
| 25 | $SCF_3$ | Cl | $CF_3$ | CCl | 2,6-$(CH_3)_2$-4-OH—Ph | 180 |
| 26 | $SOCF_3$ | Cl | $CF_3$ | CCl | 3,5-$(OCH_3)_2$-4-OH—Ph | 175 |
| 27 | $SOCF_3$ | Cl | $CF_3$ | CCl | 4-$N(CH_3)_2$—Ph | Oil |
| 28 | $SCF_3$ | Cl | $CF_3$ | CCl | Ph | 148.5 |
| 29 | $SCF_3$ | Cl | $CF_3$ | CCl | 3-$OC_2H_5$-4-OH—Ph | 151 |
| 30 | $SCF_3$ | Cl | $CF_3$ | CCl | 3,4,5-$(OCH_3)_3$—Ph | 132 |
| 31 | $SCF_3$ | Cl | $CF_3$ | CCl | 2,4-$(CH_3)_2$—Ph | 108 |
| 32 | $SCF_3$ | Cl | $CF_3$ | CCl | 4-CN—Ph | 142 |
| 33 | $SCF_3$ | Cl | $CF_3$ | CCl | 4-$NO_2$—Ph | 167.5 |
| 34 | $SCF_3$ | Cl | $CF_3$ | CCl | 4-Cl—Ph | 140 |
| 35 | $SOCF_3$ | Cl | $CF_3$ | CCl | 4-$OCH_3$—Ph | 97 |
| 36 | $SCF_3$ | Cl | $CF_3$ | CCl | 3-Cl-4-OH-5-$OCH_3$—Ph | 178 |
| 37 | $SCF_3$ | Cl | $CF_3$ | CCl | 2-Cl-4-OH—Ph | 180 |
| 38 | $SCF_3$ | Cl | $CF_3$ | CCl | 3-Cl-4-OH—Ph | 156 |
| 39 | $SCF_3$ | Cl | $CF_3$ | CCl | 2,3,5,6-$F_4$—Ph | 126 |
| 40 | $SCF_3$ | Cl | $CF_3$ | CCl | 3,4-$(OH)_2$-5-$OCH_3$—Ph | 163 |
| 41 | $SCF_3$ | Cl | $CF_3$ | CCl | 3,4-$(OCH_3)_2$—Ph | Oil |
| 42 | $SCF_3$ | Cl | $CF_3$ | CCl | 3-Br-4-OH-5-$OCH_3$—Ph | 184 |
| 43 | $SCF_3$ | Cl | $CF_3$ | CCl | 2-Cl—Ph | 159.5 |
| 44 | $SCF_3$ | Cl | $CF_3$ | CCl | 4-$NHCOCH_3$—Ph | 110 |
| 45 | $SO_2CF_3$ | Cl | $CF_3$ | CCl | 4-OH—Ph | 201 |
| 46 | $SO_2CF_3$ | Cl | $CF_3$ | CCl | 3,5-$(OCH_3)_2$-4-OH—Ph | 111 |
| 47 | $SOCF_3$ | Cl | $CF_3$ | CCl | 3-$OC_2H_5$-4-OH—Ph | 155 |
| 48 | $SOCF_3$ | Cl | $CF_3$ | CCl | 3-Cl-4-OH-5-$OCH_3$—Ph | 129.5 |
| 49 | $SCF_3$ | Cl | $CF_3$ | CCl | 4,6-$(OCH_3)_2$-2-OH—Ph | 155.5 |
| 50 | $SCF_3$ | Cl | $CF_3$ | CCl | 2-OH-3-$OCH_3$—Ph | 71 |
| 51 | $SCF_3$ | Cl | $CF_3$ | CCl | 2-F—Ph | 95 |
| 52 | $SCF_3$ | Cl | $CF_3$ | CCl | 3,5-$Br_2$-4-OH—Ph | 160.5 |
| 53 | $SCF_3$ | Cl | $CF_3$ | CCl | 4-$O_2CCH_3$—Ph | 142 |
| 54 | $SCF_3$ | Cl | $CF_3$ | CCl | 3-$OCH_3$—Ph | 99.5 |
| 55 | $SCF_3$ | Cl | $CF_3$ | CCl | 2-$CF_3$—Ph | 85.5 |
| 56 | $SCF_3$ | Cl | $CF_3$ | CCl | 3-F—Ph | 125 |
| 57 | $SCF_3$ | Cl | $CF_3$ | CCl | 4-F—Ph | 124 |
| 58 | $SCF_3$ | Cl | $CF_3$ | CCl | 3-OH—Ph | 138 |
| 59 | $SCF_3$ | Cl | $CF_3$ | CCl | 4,5-$(OCH_3)_2$-3-OH—Ph | 126 |
| 60 | $CF_3$ | Cl | $CF_3$ | CCl | 4-OH-3-$OCH_3$—Ph | 171 |
| 61 | $SO_2CF_3$ | Cl | $CF_3$ | CCl | 3-$OC_2H_5$-4-OH—Ph | 189 |
| 62 | $SCCl_2F$ | Cl | $CF_3$ | CH | 4-OH-3-$OCH_3$—Ph | 155 |
| 63 | $SCCl_2F$ | Br | $CF_3$ | CH | 4-OH-3-$OCH_3$—Ph | 147 |
| 64 | $SCF_3$ | Cl | $CF_3$ | CCl | 3,5-$(t-C_4H_9)_2$-4-OH—Ph | 183 |
| 65 | $SO_2CF_3$ | Cl | $CF_3$ | CCl | 3-OH-4-$OCH_3$—Ph | 114 |
| 66 | $SO_2CF_3$ | Cl | $CF_3$ | CCl | 4-OH-3-$CH_3$—Ph | 160d |
| 67 | $SO_2CF_3$ | Cl | $CF_3$ | CCl | 3-Cl-4-OH—Ph | 63 |
| 68 | $SO_2CF_3$ | Cl | $CF_3$ | CCl | 4-pyridyl N—O | 197d |
| 69 | $SCF_3$ | Cl | $CF_3$ | CCl | 3-$OCH_3$-4-$O_2CCH_3$—Ph | 148 |
| 70 | $SCF_3$ | Cl | $CF_3$ | CCl | 2,6-$(OCH_3)_2$—Ph | 183 |
| 71 | $SO_2CF_3$ | Cl | $CF_3$ | CCl | 3,4-$(OCH_3)_2$—Ph | 44 |
| 72 | $SO_2CF_3$ | Cl | $CF_3$ | CCl | 2,4-$(OCH_3)_2$-6-OH—Ph | 126 |
| 73 | $SO_2CF_3$ | Cl | $CF_3$ | CCl | 3,5-$(CH_3)_2$-4-OH—Ph | 210.5 |

TABLE 2A

SYNTHESIZED PYRAZOLE COMPOUNDS OF FORMULA (I), WHEREIN: $R^1$ IS CN AND $R^3$, $R^6$ AND $R^8$ ARE H (Ph = PHENYL)

| CMPD NO. | $R^2$ | $R^5$ | $R^7$ | X | $R^4$ | M.P. °C. |
|---|---|---|---|---|---|---|
| 74 | $SCF_3$ | Cl | $CF_3$ | CCl | 4-OH-5-$OCH_3$-3-$NO_2$—Ph | 165 |
| 75 | $SO_2CF_3$ | Cl | $CF_3$ | CCl | 2-Cl-4-OH—Ph | 154 |
| 76 | $SCCl_2F$ | Cl | $OCF_3$ | CCl | 4-OH—Ph | 170 |
| 77 | $SCF_3$ | Cl | $CF_3$ | CCl | 2,4-$(OCH_3)_2$-3-OH—Ph | 128 |
| 78 | $SCClF_2$ | Cl | $CF_3$ | CCl | 4-OH-3-$OCH_3$—Ph | 138 |
| 79 | $SCClF_2$ | Cl | $CF_3$ | CCl | 4-OH—Ph | 159 |
| 80 | $SCClF_2$ | Cl | $CF_3$ | CCl | 3,5-$(CH_3)_2$-4-OH—Ph | 180 |
| 81 | $SCClF_2$ | Cl | $CF_3$ | CCl | 3-OH-4-$OCH_3$—Ph | 147 |
| 82 | $SCCl_2F$ | Cl | $OCF_3$ | CCl | 3,5-$(CH_3)_2$-4-OH—Ph | 246 |
| 83 | $SCCl_2F$ | Cl | $OCF_3$ | CCl | 3-OH-4-$OCH_3$—Ph | 178 |
| 84 | $SCCl_2F$ | Cl | $OCF_3$ | CCl | 3-Cl-4-OH—Ph | 108 |

TABLE 2A-continued

SYNTHESIZED PYRAZOLE COMPOUNDS OF FORMULA (I), WHEREIN: $R^1$ IS CN AND $R^3$, $R^6$ AND $R^8$ ARE H (Ph = PHENYL)

| CMPD NO. | $R^2$ | $R^5$ | $R^7$ | X | $R^4$ | M.P. °C. |
|---|---|---|---|---|---|---|
| 85 | $SCClF_2$ | Cl | $CF_3$ | CCl | 2-Cl-4-OH—Ph | 207 |
| 86 | $SCClF_2$ | Cl | $CF_3$ | CCl | 3-Cl-4-OH—Ph | 152 |
| 87 | $SCF_3$ | Cl | $CF_3$ | N | 4-OH-3-$OCH_3$—Ph | 69 |
| 88 | $SCCl_2F$ | Cl | $OCF_3$ | CCl | 2-Cl-4-OH—Ph | 135 |
| 89 | $SCCl_2F$ | Cl | $OCF_3$ | CCl | 2,4-$(OH)_2$—Ph | 183 |
| 90 | $SCF_3$ | Cl | $CF_3$ | CCl | 2,4-$(OH)_2$-6-$CH_3$—Ph | 173 |
| 91 | $SCF_3$ | Cl | $CF_3$ | CCl | 2,3,4-$(OH)_3$—Ph | 161 |
| 92 | $SCF_3$ | Cl | $CF_3$ | CCl | 2,4,5-$(OH)_3$—Ph | 161 |
| 93 | $SCF_3$ | Cl | $CF_3$ | CCl | 3,4-$(OH)_2$-5-Br—Ph | 89 |
| 94 | $SCCl_2F$ | Cl | $CF_3$ | CCl | 3-Cl-4-OH—Ph | 148 |
| 95 | $SCCl_2F$ | Cl | $CF_3$ | N | 4-OH-3-$OCH_3$—Ph | 155 |
| 96 | $SCClF_2$ | Cl | $CF_3$ | CCl | 2,4-$(OH)_2$—Ph | 159 |
| 97 | $SCCl_2F$ | Cl | $CF_3$ | CCl | 2-Cl-4-OH—Ph | 205 |
| 98 | $SCCl_2F$ | Cl | $CF_3$ | CCl | 2,4-$(OH)_2$—h | 140 |
| 99 | $SCCl_2F$ | Cl | $CF_3$ | CCl | 3-OH-4-$OCH_3$—Ph | 104 |
| 100 | $SCF_3$ | Cl | $CF_3$ | CCl | 3-Br-4-OH—Ph | 132 |
| 101 | $SCCl_2F$ | Cl | $OCF_3$ | CCl | 3-Br-4-OH—Ph | 146 |
| 102 | $SCCl_2F$ | Cl | $OCF_3$ | CCl | 4-OH-3-$CH_3$—Ph | 151 |
| 103 | $SCCl_2F$ | Cl | $OCF_3$ | CCl | 3,5-$(OCH_3)_2$-4-OH—Ph | 158 |
| 104 | $SCCl_2F$ | Cl | $OCF_3$ | CCl | 5-Br-4-OH-3-$OCH_3$—Ph | 216 |
| 105 | $SCCl_2F$ | Cl | $OCF_3$ | CCl | 4,5-$(OH)_2$-3-$OCH_3$—Ph | 197 |
| 106 | $SCCl_2F$ | Cl | $OCF_3$ | CCl | 3-$OC_2H_5$-4-OH—Ph | 169.5 |
| 107 | $SO_2CH_3$ | Cl | $CF_3$ | CCl | 4-OH-3-$OCH_3$—Ph | 215 |
| 108* | $NO_2$ | Cl | $CF_3$ | CCl | 4-OH-3-$OCH_3$—Ph | 125 |
| 109* | $SOCF_3$ | Cl | $CF_3$ | CCl | 4-OH-3-$OCH_3$—Ph | 188 |
| 110 | $SCH_3$ | Cl | $CF_3$ | CCl | 4-OH-3-$OCH_3$—Ph | Oil |
| 111 | $SCH_3$ | Cl | $CF_3$ | CCl | 4-OH—Ph | 178 |

*$R^1$ is Cl.

TABLE 2B

SYNTHESIZED PYRAZOLE COMPOUNDS OF FORMULA (I), WHEREIN: $R^1$ IS CN AND $R^3$, $R^6$ AND $R^8$ ARE H (Ph = PHENYL)

| CMPD NO. | $R^2$ | $R^5$ | $R^7$ | X | $R^4$ | M.P. °C. |
|---|---|---|---|---|---|---|
| 112 | $SCF_3$ | Cl | $CF_3$ | CCl | 3,5-$(CF_3)_2$—Ph | 110 |
| 113 | $SCF_3$ | Cl | $CF_3$ | CCl | 2-$OCH_3$—Ph | 141 |
| 114 | $SCF_3$ | Cl | $CF_3$ | CCl | 2-Cl-6-F—Ph | 160 |
| 115 | $SCF_3$ | Cl | $CF_3$ | CCl | 2-imidazolyl | 224 |
| 116 | $SCF_3$ | Cl | $CF_3$ | CCl | 3-CN—Ph | 104 |
| 117 | $SCF_3$ | Cl | $CF_3$ | CCl | 2-OH-4-$N(C_2H_5)_2$—Ph | 58 |
| 118 | $SCF_3$ | Cl | $CF_3$ | CCl | 3-$OCH_3$-4-$OC_{10}H_{21}$—Ph | 123 |
| 119 | $SCF_3$ | Cl | $CF_3$ | CCl | 4-$OC_5H_{11}$—Ph | 64 |
| 120 | $SCF_3$ | Cl | $CF_3$ | CCl | 3-$OCH_3$-4-$OCH_2Ph$—Ph | 123 |
| 121 | $SCF_3$ | Cl | $CF_3$ | CCl | 3-$OCH_3$-4-$O_2CC_7H_{15}$—Ph | Oil |
| 122 | $SCCl_2F$ | Cl | $OCF_3$ | CCl | 3,4-$(OCH_3)_2$—Ph | 85 |
| 123 | $SCCl_2F$ | Cl | $OCF_3$ | CCl | 3,4,5-$(OCH_3)_3$—Ph | 134 |
| 124 | $SCCl_2F$ | Cl | $OCF_3$ | CCl | 2-OH—Ph | 137 |
| 125 | $SCCl_2F$ | Cl | $OCF_3$ | CCl | 2-OH-3-$OCH_3$—Ph | 125 |
| 126 | $SCH_3$ | Cl | $CF_3$ | CCl | Ph | 156 |

EXAMPLE 6

Miticide, Insecticide, Aphicide, and Nematicide Use

The following representative test procedures, using compounds of the invention, were conducted to determine the pesticidal use and activity of compounds of the invention against: mites; certain insects, including aphids, two species of caterpillar, a fly, and three species of beetle larvae (one foliar feeding and two root feeding); and nematodes. The specific species tested were as follows:

| GENUS, SPECIES | COMMON NAME | (ABBREVIATION) |
|---|---|---|
| Tetranychus urticae | twospotted spider mite | TSM |
| Aphis nasturtii | buckthorn aphid | BA |
| Spodoptera eridania | southern armyworm | SAW |
| Epilachna varivestis | Mexican bean beetle | MBB |
| Musca domestica | housefly | HF |
| Diabrotica u. howardi | southern corn rootworm | SCRW |
| Diabrotica virgifera | western corn rootworm | WCRW |
| Meloidogyne incognita | southern root-knot nematode | SRKN |
| Aphis gossypii | cotton aphid | CA |
| Schizaphis graminum | greenbug (aphid) | GB |
| Heliothis virescens | tobacco budworm | TBW |

Formulations

The test compounds were formulated for use according to the following methods used for each of the test procedures.

For mite, aphid, southern armyworm, Mexican bean beetle, and tobacco budworm tests, a solution or suspension was prepared by adding 10 mg of the test compound to a solution of 160 mg of dimethylformamide, 838 mg of acetone, 2 mg of a 3:1 ratio of Triton X-72: Triton X-152 (respectively, mainly anionic and nonionic low foam emulsifiers which are each anhydrous blends of alkylaryl polyether alcohols with organic sulfonates), and 98.99 g of water. The result was a concentration of 100 ppm of the test compound.

For housefly tests, the formulation was initially prepared in a similar manner to the above, but in 16.3 g of water with corresponding adjustment of other components, providing a 200 ppm concentration. Final dilution with an equal volume of a 20% by weight aqueous solution of sucrose provided a 100 ppm concentration of the test compound. When necessary, sonication was provided to insure complete dispersion.

For southern and western corn rootworm tests, a solution or suspension was prepared in the same manner as that used for the initial 200 ppm concentration for housefly. Aliquots of this 200 ppm formulation were then used by dilution with water according to the required test concentration.

For southern root-knot nematode and systemic tests for southern armyworm, cotton aphid, tobacco budworm and greenbug, a stock solution or suspension was prepared by adding 15 mg of the test compound to 250 mg of dimethylformamide, 1250 mg of acetone and 3 mg of the emulsifier blend referenced above. Water was then added to provide a test compound concentration of 150 ppm. When necessary, sonication was provided to insure complete dispersion.

For tobacco budworm contact tests, a stock solution was prepared by dissolving the compound in acetone and then further diluted to provide the required serial dilution concentrations.

Test Procedures

The above formulated test compounds were then evaluated for their pesticidal activity at the specified concentrations, in ppm (parts per million) by weight, according to the following test procedures:

Twospotted spider mite: Leaves infested with adult and nymphal stages of the two-spotted spider mite, obtained from a stock culture were placed on the primary leaves of two bean plants growing in a 6 cm. peat pot. A sufficient number of mites (150–200) for testing were transferred to the fresh plants within a period of twenty-four hours. The potted plants (one pot per compound) were placed on a revolving turntable and sprayed, sufficient to wet the plants to runoff, with 100 ml of the 100 ppm test compound formulation by use of a DeVilbiss spray gun set at 40 psig. air pressure. As an untreated control, 100 ml of the water-acetone-DMF-emulsifier solution, containing no test compound, were also sprayed on infested plants. A treated control with a commercial technical compound, either dicofol or hexythiazox, formulated in the same manner, was tested as a standard. The sprayed plants were held for six days, after which a mortality count of motile forms was made.

Twospotted spider mite (ovicide test): Eggs were obtained from adults of the twospotted spider mite from a stock culture. Heavily infested leaves from the stock culture were placed on uninfested bean plants. Females were allowed to oviposit for a period of about 24 hours, after which the leaves of the plant were dipped into a solution of TEPP (tetraethyl diphosphate) in order to kill the motile forms and prevent additional egg laying. This dipping procedure, which was repeated after the plants dried, did not affect the viability of the eggs. The potted plants (one pot per compound) were placed on a revolving turntable and sprayed, sufficient to wet the plants to runoff, with 100 ml of the 100 ppm test compound formulation by use of a DeVilbiss spray gun set at 40 psig. air pressure. As an untreated control, 100 ml of the water-acetone-DMF-emulsifier solution, containing no test compound, were also sprayed on infested plants. A treated control with a commercial technical compound, typically demeton, formulated in the same manner, was tested as a standard. The sprayed plants were held for seven days, after which a mortality count of egg forms was made along with notations on residual activity on hatched larvae.

Buckthorn or cotton aphid: Adult and nymphal stages of buckthorn or cotton aphid were reared on potted dwarf nasturtium or cotton plants, respectively. The potted plants (one pot per compound tested) infested with 100–150 aphids, were placed on a revolving turntable and sprayed with 100 ml of the 100 ppm test compound formulation by use of a DeVilbiss spray gun set at 40 psig air pressure. As an untreated control, 100 ml of a water-acetone-DMF-emulsifier solution, containing no test compound, were also sprayed on infested plants. A treated control with a commercial technical compound, malathion or cyhalothrin, formulated in the same manner, was tested as a standard. After spraying, the pots were stored for one day on buckthorn aphid or three days for cotton aphid, after which the dead aphids were counted.

Southern armyworm: Potted bean plants, were placed on a revolving turntable and sprayed with 100 ml of the 100 ppm test compound formulation by use of a DeVilbiss spray gun set at 40 psig air pressure. As an untreated control, 100 ml of a water-acetone-DMF-emulsifier solution, containing no test compound, were also sprayed on plants. A treated control with a commercial technical compound, either cypermethrin or sulprofos, formulated in the same manner, was tested as a standard. When dry, the leaves were placed in plastic cups lined with moistened filter paper. Five randomly selected second instar southern armyworm larvae were introduced into each cup which was closed and held for five days. Larvae which were unable to move the length of the body, even upon stimulation by prodding, were considered dead.

Tobacco budworm: Potted cotton plants were placed on a revolving turntable and sprayed with 100 ml of the 100 ppm test compound formulation by use of a DeVilbiss spray gun set at 40 psig air pressure. As an untreated control, 100 ml of a water-acetone-DMF-emulsifier solution, containing no test compound, were also sprayed on plants. A treated control with a commercial technical compound, either cypermethrin or sulprofos, formulated in the same manner, was tested as a standard. When dry, the leaves were placed in plastic dishes containing a piece of filter paper and a moistened dental wick. One randomly selected second instar tobacco budworm larva was then introduced into each cup which was closed and held for five days. Larvae unable to move the length of their body, even upon stimulation by prodding, were considered dead.

Mexican bean beetle: Potted bean plants were placed on a revolving turntable and sprayed with 100 ml of the 100 ppm test compound formulation, sufficient to wet the plants to runoff, by use of a DeVilbiss spray gun set at 40 psig air pressure. As an untreated control, 100 ml of a water-acetone-DMF-emulsifier solution, containing no test compound, were also sprayed on plants. A treated control with a commercial technical compound, either cypermethrin or sulprofos, formulated in the same manner, was tested as a standard. When dry, the leaves were placed in plastic cups lined with moistened filter paper. Five randomly selected second instar Mexican bean beetle larvae were introduced into each cup which was closed and held for five days. Larvae which were unable to move the length of the body, even upon stimulation by prodding, were considered dead.

House fly: Four to six day old adult house flies were reared according to the specifications of the Chemical Specialties Manufacturing Association (Blue Book, McNair-Dorland Co., N.Y. 1954; pages 243–244, 261) under controlled conditions. The flies were immobilized by anesthetizing with carbon dioxide and twenty five immobilized individuals, males and females, were transferred to a cage consisting of a standard food strainer and a wrapping-paper-covered surface. Ten ml of the 100 ppm test compound formulation were added to a souffle cup containing an absorbent cotton pad. As an untreated control, 10 ml of a water-acetone-DMF-emulsifier-sucrose solution, containing no test compound, were applied in a similar manner. A treated control with a commercial technical compound, malathion, formulated in the same manner, was tested as a standard. The bait cup was introduced inside the food strainer prior to admitting the anesthetized flies. After 24 hours, flies which showed no sign of movement on stimulation were considered dead.

Southern or western corn rootworm: Into a jar containing 60 g of sandy loam soft was added 1.5 ml of an aqueous formulation consisting of an aliquot of the 200 ppm test compound formulation, diluted with water as appropriate for the final soil concentration of the test compound, 3.2 ml of water and five pregerminated corn seedlings. The jar was shaken thoroughly to obtain an even distribution of the test formulation. Following this, twenty corn rootworm eggs (or optionally ten first instar larvae in the case of WCRW) were placed into a cavity, which was made in the soil. Vermiculite (1 ml), used optionally in the case of WCRW tests, and water (1.7 ml) were then added to this cavity. In a similar manner, an untreated control was prepared by application of the same size aliquot of a water-acetone-DMF-emulsifier solution, containing no test compound. Additionally, a treated control with a commercial technical compound (selected typically from terbufos, fonofos, phorate, chlorpyrifos, carbofuran, isazophos, or ethoprop), formulated in the same manner was used as needed as a test standard. After 7 days, the living rootworm larvae were counted using a well known "Berlese" funnel extraction method.

Southern root-knot nematode: Infected roots of tomato plants, containing egg masses of southern root-knot nematode, were removed from a stock culture and cleaned of soil by shaking and washing with tap water. The nematode eggs were separated from the root tissue and rinsed with water. Samples of the egg suspension were placed on a fine screen over a receiving bowl, in which the water level was adjusted to be in contact with the screen. From the bowl, juveniles were collected on a fine screen. The bottom of a cone-shaped container was plugged with coarse vermiculite and then filled to within 1.5 cm of the top with about a 200 ml volume of pasteurized soil. Then into a hole made in the center of the soil in the cone was pipetted an aliquot of the 150 ppm test compound formulation. A treated control with a commerical technical compound, fenamifos, formulated in a similar manner, was tested as a standard. As an untreated control, an aliquot of a water-acetone-DMF-emulsifier solution, containing no test compound, was applied in a similar manner. Immediately after treatment of the soil with the test compound there were added to the top of each cone 1000 second stage juvenile southern root-knot nematodes. After 3 days, a single healthy tomato seedling was then transplanted into the cone. The cone, containing the infested soil and tomato seedling, was kept in the greenhouse for 3 weeks. At the termination of the test, roots of the tomato seedling were removed from the cone and evaluated for galling on a rating scale relative to the untreated control as follows:

1—severe galling, equal to untreated control
3—light galling
4—very light galling
5—no galling, ie, complete control These results were then converted to an $ED_3$ or $ED_5$ value (effective dose to provide a 3 or 5 gall rating).

Southern armyworm on tomato - systemic evaluation: This test was conducted in conjunction with the southern root-knot nematode evaluation (discussed below). The tomato plants, grown in the soil (at an initial compound test screening rate of 6.6 ppm soil concentration or about 150 ppm solution concentration) for nematode evaluation, were then utilized for evaluation of a compound's uptake via roots and subsequent systemic transport to the tomato foliage. At the termination of the nematode test, 21 days after treatment, the tomato foliage was excised, placed into a plastic container, and infested with second instar larvae of southern armyworm. After about 5 days, the larvae were examined for percent mortality.

Cotton aphid and tobacco budworm (on cotton) and greenbug and tobacco budworm (on Sorghum) - systemic evaluation: A 7.0 ml aliquot of the 150 ppm nematode test solution was applied to deliver the equivalent of 10.0 ppm soil concentration dose as a drench to 6 cm pots containing cotton and sorghum plants. The cotton plants were previously infested with cotton aphids about two days before treatment and greenbug one day before treatment. After holding the plants about three days, the plants were rated for aphid activity. Again at six days, the plants were rated for aphid activity and the cotton aphids and greenbugs were counted and mortality was assessed. Portions of the cotton and sorghum foliage were excised, placed in separate plastic containers, and infested with second instar larvae of tobacco budworm. The potted plants were dipped in sulfotepp to kill the remaining aphids and returned to the greenhouse for regrowth. Thirteen days after treatment, the remaining foliage was excised and fed to tobacco budworms. Mortality was assessed six days after infestation.

Cotton aphid and southern armyworm (on cotton) and greenbug and Southern armyworm (on sorghum) - systemic evaluation: A stock solution or suspension was prepared to deliver 5 ml of a 20 ppm soil concentration dose (and subsequent dilutions) as a drench to 6 cm pots containing cotton and sorghum plants. The cotton plants were previously infested with cotton aphids about two days before treatment and greenbug one day before treatment. After holding the plants about three days, the plants were rated for aphid activity. Again at six days, the plants were rated for aphid activity and the cotton aphids and greenbugs were counted and mortality was assessed. Portions of the cotton and sorghum foliage were excised, placed in separate plastic containers, and infested with second instar larvae of southern armyworms. The potted plants were dipped in sulfotepp to kill the remaining aphids and returned to the greenhouse for regrowth. Thirteen days after treatment the remaining foliage was excised and fed to southern armyworm. Mortality was assessed six days after infestation.

Cotton aphid and southern armyworm (on cotton and oats) - seed treatment evaluation: Technical material was applied to the seed of oats and cotton by placing the compound and the seed in an appropriate sized jar and rolling the jar on a ball mill. Assay of the material applied to the seed was by weight. Seed was then planted. When germinated and emerged, the plants were infested at the appropriate intervals with host insects. Mortality was assessed on those insects.

Tobacco budworm - contact evaluation: The following topical application method provides an assessment of contact toxicity of a compound to tobacco budworm larvae. The test compound solution at sequential two-fold dilution concentrations from 10 down to 0.16 $\mu g/\mu l$ was applied by a microinjector in replicated 1 $\mu l$ portions to the dorsum of approximately 20 mg tobacco budworm larvae. This is equivalent to applied doses of 500 down to 8 $\mu g/g$ body weight. An acetone treated control, without any test compounds, was also applied. A treated control with a commercial technical compound, cypermethrin or thiodicarb, also in acetone was used as a standard. The treated larvae were placed, individually, in separate plastic petri dishes containing an untreated cotton leaf and a moist dental wick. The treated larvae were maintained at about 27° C. and 50% relative humidity. The percent mortality was rated 1 and 4 days after treatment.

Use Results: Typical results of miticidal, insecticidal, and nematicidal activity for some of the representative compounds of the invention are discussed below or the results of some compounds are set forth in TABLE 3 against the indicated test species (BA*/CA, SAW, MBB, HF, TBW, SCRW*/WCRW: designated by common name abbreviations) and at the indicated dosage rates. The results in TABLE 3 are presented (by an X) as compounds which provide a 70-100% mortality against the indicated test species.

Some of the compounds of the invention are also acaricides where, for example, CMPD NO's 40, 47, and 57 provided 30-70% control of mites at 100 ppm in foliar bait tests.

Some of the compounds additionally exhibit systemic control of insect larvae and aphids via root uptake at the soil concentrations specified in the above protocols. Some, for example, are as follows: 50-100% control of southern armyworm on tomato (CMPD NO's 10, 11 and 12); 30-100% control of southern armyworm at six days on cotton (CMPD NO's 69, 89, 113 and 120) and 30-100% control of southern armyworm at thirteen days (CMPD NO's 64, 65, 67, 68 and 110); 30-100% control of southern armyworm after six days on sorghum (CMPD NO's 2, 10, 69, 72, 90, 100, 115 and 121) and 70-100% control at thirteen days (CMPD NO's 65, 66, 110 and 117); 100% control of tobacco budworm after six days on sorghum (CMPD NO's 16, 17, 18, 19 and 20); 30-100% control of cotton aphid after six days on cotton (CMPD NO's 13, 16, 17, 18, 19, 107, 110, 111, 112 and 126); and 30-100% control of greenbug after six days on sorghum (CMPD NO's 4, 16, 17, 18, 19, 20, 21, 74, 87, 90, 93, 107, 110, 111, 112 and 126).

Some of the compounds also provide activity via seed treatment where, for example. CMPD NO, 2, at 1.0 wt. % on oat seeds, provided 100% control of southern armyworm after six days.

Compounds of the invention also provide surprising, unexpected and excellent control of tobacco budworm (TBW) when applied in topical or contact tests where, for example, CMPD NO's 1-6, 9-11, 13, 15-19, 21-32, 35-38, 40, 42, 44-47, 50, 52, 58, 59, 61, 65-67, 69, 71, 73-78, 80, 81, 84-89, 91-94, 96-103 and 116 provide 50-100% control at an application dose of 63 $\mu g/g$ body weight.

Nematicidal activity is additionally provided by compounds of the invention where, for example, CMPD NO's 7, 10 and 89 gave ED$_3$ value on SRKN larvae of about 21 kg/ha and CMPD NO's 7, 9 and 11 gave ED$_3$ values on SRKN eggs of between about 14 to 21 kg/ha.

Furthermore, compounds of the invention exhibit reduced or antifeeding properties for some pest species, for example for foliar pests such as southern armyworm and Mexican bean beetle.

The compounds of the invention have utility against various pest species at even lower rates, for example: for foliar application, rates in the range of about 50-0.5 ppm, or less, may be useful; for bait application, rates in the range of about 50-0.05 ppm, or less, may be useful; and for soil application, rates in the range of about 1.0-0.01 ppm, or less, may be useful.

In the above discussion and the results reported in TABLE 3, compounds according to the invention are applied at various concentrations. The use of a 1 ppm (concentration of the compound in parts per million of the test solution applied) foliar solution or suspension or emulsion corresponds approximately to an application of 1 g/ha of active ingredient, based upon an approximate spray volume of 1000 liters/ha (sufficient to run off). Thus applications of foliar sprays of from about 6.25 to 500 ppm would correspond to about 6-500 g/ha. For soil applications, a 1 ppm soil concentration, on the basis of about a 7.5 cm soil depth, corresponds to an approximate 1000 g/ha broadcast field application. Or alternatively stated, a 1 ppm soil concentration as above, but as an approximate 18 cm band application corresponds to an approximate 166 g/ha. For the contact test, it is approximated that an application dose of 10 $\mu g/\mu l$ body weight applied as a 0.2 $\mu g/\mu l$ (200 ppm) solution to the larvae would correspond to a field use application as a broadcast spray at about 50 to about 100 g/ha.

TABLE 3

USE EXAMPLE OF PESTICIDAL ACTIVITY OF REPRESENTATIVE PYRAZOLE COMPOUNDS OF FORMULA (I) PROVIDING 70-100% PEST MORTALITY

| CMPD. NO. | Foliar or Bait Application at 100 ppm | | | | | Soil conc.-.5 ppm SCRW*/WCRW |
|---|---|---|---|---|---|---|
| | BA*/CA | SAW | MBB | HF | TBW | |
| 1 | | X | X | X | X | X* |
| 2 | | X | X | X | X | |
| 3 | | X | X | X | X | X* |
| 4 | X* | X | X | X | X | X* |

TABLE 3-continued

USE EXAMPLE OF PESTICIDAL ACTIVITY OF REPRESENTATIVE PYRAZOLE COMPOUNDS OF FORMULA (I) PROVIDING 70–100% PEST MORTALITY

| CMPD. NO. | Foliar or Bait Application at 100 ppm | | | | | Soil conc.-.5 ppm |
|---|---|---|---|---|---|---|
| | BA*/CA | SAW | MBB | HF | TBW | SCRW*/WCRW |
| 5 | | X | | X | X | X* |
| 6 | | X | X | X | X | |
| 8 | X* | X | X | X | X | |
| 9 | | X | X | X | X | |
| 10 | X* | X | | X | X | X |
| 11 | X* | X | X | X | X | X |
| 12 | X* | X | | X | X | X |
| 13 | X | X | X | X | X | |
| 14 | | X | | | X | |
| 15 | X | X | X | X | X | |
| 16 | X | X | X | X | X | |
| 17 | X | X | X | X | X | |
| 18 | X | X | X | X | X | |
| 19 | | X | | X | X | |
| 20 | X | X | X | X | X | |
| 21 | X | X | X | X | X | |
| 22 | X | X | X | X | X | |
| 23 | | X | X | X | | X |
| 24 | | X | | X | X | X |
| 25 | | X | | X | | |
| 26 | X | X | X | X | | X |
| 27 | | X | | X | | X |
| 28 | X | X | | X | X | X |
| 29 | | X | | X | X | X |
| 30 | | X | | X | | X |
| 31 | | X | | | | X |
| 32 | X | X | X | X | | X |
| 33 | X | X | | X | | |
| 34 | X | X | | X | | X |
| 35 | | X | X | X | | X |
| 36 | X | X | | X | X | |
| 37 | X | X | | X | X | X |
| 38 | X | X | | X | X | X |
| 39 | X | X | | X | X | X |
| 40 | X | X | | X | X | |
| 42 | X | X | | X | X | |
| 43 | X | X | | X | | |
| 44 | | X | | X | | X |
| 46 | | X | | X | | |
| 47 | X | X | | X | | X |
| 48 | X | X | X | X | | |
| 49 | X | X | | X | | |
| 50 | | X | X | X | | |
| 51 | X | X | X | X | | |
| 52 | X | X | X | X | | |
| 53 | X | X | X | X | | |
| 54 | X | X | X | X | | |
| 55 | | X | | X | | |
| 56 | X | X | | X | | |
| 57 | X | X | | X | | |
| 58 | | X | | X | | |
| 59 | X | X | | X | | |
| 60 | X | X | | X | | |
| 61 | | X | X | X | | |
| 62 | | X | X | X | X | |
| 63 | | X | X | X | X | |
| 64 | X | | | X | | |
| 65 | X | X | X | X | | X |
| 66 | | X | X | X | X | |
| 67 | | X | | X | X | X |
| 68 | | | X | X | | |
| 69 | X | X | | X | X | |
| 70 | | X | | | X | |
| 71 | | | X | X | X | |
| 73 | | X | X | X | X | X |
| 74 | X | X | X | X | X | X |
| 75 | | X | X | X | X | |
| 76 | | X | X | X | X | |
| 77 | X | X | X | X | X | |
| 78 | | X | | X | X | X |
| 79 | | X | | X | X | X |
| 80 | X | X | X | X | | X |
| 81 | | X | X | X | X | X |
| 82 | | X | | X | X | |
| 83 | | X | X | X | X | |
| 84 | | X | X | X | X | X |

TABLE 3-continued

USE EXAMPLE OF PESTICIDAL ACTIVITY OF REPRESENTATIVE
PYRAZOLE COMPOUNDS OF FORMULA (I) PROVIDING 70-100%
PEST MORTALITY

| CMPD. NO. | Foliar or Bait Application at 100 ppm | | | | | Soil conc.-.5 ppm |
|---|---|---|---|---|---|---|
| | BA*/CA | SAW | MBB | HF | TBW | SCRW*/WCRW |
| 85 | X | X | | X | | |
| 86 | | X | | X | X | |
| 87 | X | X | X | X | | |
| 88 | | X | | X | X | |
| 89 | | X | X | X | | |
| 90 | X | X | | X | X | |
| 91 | X | X | | X | X | |
| 92 | X | X | | X | X | |
| 93 | | | | X | | |
| 94 | | X | X | X | X | |
| 96 | | X | X | X | | |
| 97 | | | | X | X | |
| 98 | | X | X | X | | |
| 99 | | | | X | X | |
| 100 | X | X | X | X | | |
| 101 | | X | | X | | |
| 102 | | X | | X | | |
| 103 | | X | | X | | |
| 104 | | X | | X | | X |
| 105 | | X | | X | | |
| 106 | | | X | X | | |
| 107 | | | X | X | | |
| 108 | | | | X | | |
| 109 | | | | X | X | |
| 110 | | | | X | | |
| 111 | | | | X | | |
| 112 | X | X | | X | X | X |
| 113 | X | X | X | X | X | |
| 114 | X | X | | X | X | X |
| 115 | | X | X | X | X | |
| 116 | X | X | X | X | X | |
| 117 | | X | | X | | |
| 118 | | X | | X | X | |
| 119 | | X | | X | X | |
| 120 | | X | | X | X | |
| 121 | | X | | X | X | |
| 122 | | X | | X | | |
| 123 | X | X | X | X | | |
| 124 | X | X | | X | | |
| 125 | | X | | X | | |
| 126 | | | | X | | |

METHODS AND COMPOSITIONS

As is evident from the foregoing pesticidal uses, the present invention provides pesticidally active compounds and methods of use of said compounds for the control of a number of pest species which includes: arthropods, especially insects or mites; plant nematodes; or helminth or protozoan pests. The compounds thus are advantageously employed in practical uses, for example, in agricultural or horticultural crops, forestry, veterinary medicine or livestock husbandry, or in public health.

A feature of the present invention therefore provides a method of control of pests at a locus which comprises the treatment of the locus (e.g., by application or administration) with an effective amount of a compound of general formula (I) and more preferably a compound of formula (Ia), wherein the substituent groups are as hereinbefore defined. The locus includes, for example, the pest itself or the place (plant, animal, person, field, structure, premises, forest, orchard, waterway, soil, plant or animal product, or the like) where the pest resides or feeds.

The compounds of this invention are preferably used to control soil insects, such as corn rootworm, termites (especially for protection of structures), root maggots, wireworms, root weevils, stalkborers, cutworms, root aphids, or grubs. They may also be used to provide activity against plant pathogenic nematodes, such as root-knot, cyst, dagger, lesion, or stem or bulb nematodes, or against mites. For the control of soil pests, for example corn rootworm, the compounds are advantageously applied to or incorporated at an effective rate into the soil in which crops are planted or to be planted or to the seeds or growing plant roots.

Furthermore, these compounds may be useful in the control via foliar application or systemic action of some arthropods, especially insects or mites, which feed on the above ground portions of plants. Control of foliar pests may additionally be provided by application to the plant roots or plant seeds with subsequent systemic translocation to the above ground portions of the plants.

In the area of public health, the compounds are especially useful in the control of many insects, especially filth flies or other Dipteran pests, such as houseflies, stableflies, soldierflies, hornflies, deerflies, horseflies, midges, punkies, blackflies, or mosquitoes.

Compounds of the invention may be used in the following applications and on the following pests including arthropods, especially insects or mites, nematodes, or helminth or protozoan pests:

In the protection of stored products, for example cereals, including grain or flour, groundnuts, animal feedstuffs, timber or household goods, e.g. carpets and textiles, compounds of the invention are useful against attack by arthropods, more especially beetles, including weevils, moths or mites, for example Ephestia spp. (flour moths), Anthrenus spp. (carpet beetles), Tribolium spp. (flour beetles), Sitophilus spp. (grain weevils) or Acarus spp. (mites).

In the control of cockroaches, ants or termites or similar arthropod pests in infested domestic or industrial premises or in the control of mosquito larvae in waterways, wells, reservoirs or other running or standing water.

For the treatment of foundations, structures or soil in the prevention of the attack on building by termites, for example, Reticulitermes spp., Heterotermes spp., Coptotermes spp..

In agriculture against adults, larvae and eggs of Lepidoptera (butterflies and moths), e.g. Heliothis spp. such as *Heliothis virescens* (tobacco budworm), *Heliothis armigera* and *Heliothis zea*, Spodoptera spp. such as *S. exempta, S. frugiperda, S. exiqua, S. littoralis* (Egyptian cotton worm), *S. eridania* (southern army worm), and *Mamestra configurata* (bertha army worm); Earias spp. e.g. *E. insulana* (Egyptian bollworm), *Pectinophora spp.* e.g. *Pectinophora gossypiella* (pink bollworm), Ostrinia spp. such as *O. nubilalis* (European cornborer), *Trichoplusia ni* (cabbage looper), Artogeia spp. (cabbage worms), Laphygma spp. (army worms), Agrotis and Amathes spp. (cutworms), Wiseana spp. (porina moth), Chilo spp. (rice stem borer), Tryporyza spp. and Diatraea spp. (sugar cane borers and rice borers), *Spargano- this pilleriana* (grape berry moth), *Cydia pomonella* (codling moth), Archips spp. (fruit tree tortrix moth), Plutella xylostella (diamond back moth), *Bupalus piniarius, Cheimatobia brumata, Lithocolletis blancardella, Hyponomeuta padella, Plutella maculipennis, Malacosoma neustria, Euproctis chrysorrhoea,* Lymantria spp. *Bucculatrix thurberiella, Phyllocnistis citrella,* Euxoa spp., *Feltia brassicae, Panolis flammea, Prodenia litura, Carpocapsa pomonella, Pyrausta nubilalis. Ephestia kuehniella, Galleria mellonella, Tineola bisselliella, Tinea pellionella, Hofmannophila pseudospretella, Cacoecia podana, Capus reticulana, Choristoneura fumiferana, Clysia ambiguellis, Homona magnanime* and *Tortix viridana*.

Against adults and larvae of Coleoptera (beetles) e.g. *Hypothenemus hampei* (coffee berry borer), Hylesinus spp. (bark beetles), Anthonomus spp. e.g. grandis (cotton boll weevil), Acalymma spp. (cucumber beetles), Lema spp., Psylliodes spp,, *Leptinotarsa decemlineata* (Colorado potato beetle), Diabrotica spp. (corn rootworms), Gonocephalum spp. (false wire worms), Agriotes spp., Limonius spp. (wireworms), Dermolepida spp., Popillia spp., Heteronychus spp. (white grubs), *Phaedon cochleariae* (mustard beetle), Epitrix spp. (flea beetles), *Lissorhoptrus oryzophilus* (rice water weevil), Meligethes spp. (pollen beetles), Ceutorhynchus spp., Rhynchoporus and Cosmopolites spp. (root weevils), *Anobiumn punctatum, Rhizopertha dominica, Bruchidius obtectus, Acanthoscelides obtectus, Hylotrupes bajulus, Agelastica alni, Psylliodes chrysocephala, Epilachna varivestis,* Atomaria spp., *Oryzaephilus surinamensis,* Sitophilus spp., *Otiorrhynchus sulcatus, Cosmoplites sordidus, Ceuthorrhynchus assimilis, Hypera postica,* Dermestes spp., Trogoderma spp., Anthrenus spp., Attagenus spp., Lyctus spp., *Maligethes aeneus,* Ptinus spp., *Niptus hololeucrus, Gibbium psylloides,* Tribolium spp., *Tenebrio molitor,* Conoderus spp., *Melolontha melolontha, Amphimallon solststialis* and *Costelytra zealandica.*

Against Heteroptera (Hemiptera and Homoptera) e.g. Psylla spp., Bemisia spp., Trialeurodes spp., Aphis spp., Myzus spp., *Megoura viciae,* Phylloxera spp., Adelges spp., *Phorodon humuli* (hop damson aphid), Aeneolamia spp., Nephotettix spp. (rice leaf hoppers), Empoasca spp., Nilaparvata spp., Perkinsiella spp., Pyrilla spp., Aonidiella spp. (red scales), Coccus spp., Pseucoccus spp., Helopeltis spp. (mosquito bugs), Lygus spp., Dysdercus spp., Oxycarenus spp., Nezara spp., Eurygaster spp., *Piesma quadrata, Cimex lectularius, Rhodnius prolixus* and Triatoma spp. *Aspidiotus hederae, Aeurodes brassicae, Brevicoryne brassicae, Cryptomyzus ribis, Doralis fabae, Doralis pomi., Eriosoma lanigerum, Hyalopterus arundinis, Macrosiphum avenae, Phorodon humuli, Rhopalosiphum padi, Euscelis bilobatus, Nephotettix cincticeps, Lecanium corni, Saissetia oleae, Laodelphax striatellus.*

Against Hymenoptera e.g. Athalia spp. and Cephus spp. (saw flies), Atta spp. (leaf cutting ants), Diprion spp., Hopolocampa spp., Lasius spp., Monomorium spp., Polistes spp., Vespa spp., Vespula spp., and Solenopsis spp..

Against Diptera e.g. Delia spp. (root maggots), Atherigona spp. and Chlorops spp., Sarcophaga spp., Musca spp, Phormia spp., Aedes spp., Anopheles spp., Simulium spp., (shoot flies), Phytomyza spp. (leaf miners), Ceratitis spp. (fruit flies), Culex spp., *Drosophila melanogaster, Ceratitis capitata, Dacus oleae, Tipula paludosa, Calliphora erythrocephala,* Lucilia spp.. Chrysomyia spp., Cuterebra spp., Gastrophilus spp., Hyppobosca spp., Stomoxys spp., Oestrus spp., Hypoderma spp., Tabanus spp., Fannia spp., *Bibio hortulanus, Oscinella frit,* Phorbia spp., *Pegomyia hyoscyani.*

Against Thysanoptera such as *Thrips tabaci, Hercinothrips femoralis,* and Frankliniella spp..

Against Orthoptera such as Locusta and Schistocerca spp., (locusts and crickets) e.g. Gryllus spp., and Acheta spp. for example, *Blatta orientalis, Periplaneta americana, Leucophaea maderae, Blatella germanica, Acheta domesticus,* Gryllotalpa spp., *Locusta migratoria migratorioides, Melanoplus differentialis* and Schistocerca gregaria.

Against Collembola e.g. Sminthurus spp. and Onychiurus spp. (springtails); Periplaneta spp. and Blattela spp. (roaches).

Against Isoptera e.g. Odontotermes spp., Reticuletermes spp., Coptotermes spp. (termites).

Against Dermaptera e.g. Forticula sp. (earwigs).

Against arthropods of agricultural significance such as Acari (mites) e.g. Tetranychus spp., Panonychus spp., Bryobia spp. (spider mites), Ornithonyssus spp. (fowl mites), Eriophyes spp. (gall mites), and Polyphadotarsonemus supp..

Against Thysanura, for example *Lepisma saccharia.*

Against Anoplura for example, *Phylloxera vastatrix,* Pemphigus spp., *Pediculus humanus corporis,* Haematopinus spp. and Linognathus spp..

Against Mallophaga, for example, Trichodectes spp. and Damalinea spp..

Against Siphonoptera, for example, *Xenopsylla cheopis* and Ceratophyllus spp..

Against other arthropods, such as Blaniulus spp. (millipedes), Scutigerella spp. (symphilids), Oniscus spp. (woodlice) and Triops spp. (crustacea).

Against Isopoda, for example, *Oniseus asellus, Armadillidium vulgare* and *Porcellio scaber.*

Against Chilopoda, for example, *Geophilus carpophagus* and Scutigera spex..

Against nematodes which attack plants or trees of importance to agriculture, forestry or horticulture either directly or by spreading bacterial, viral, mycoplasma or fungal diseases of the plants. For example root-knot nematodes such as Meloidogyne spp. (e.g. *M. incognita*); cyst nematodes such as Globodera spp. (e.g. *G. rostochiensis*); Heterodera spp. (e.g. *H. avenae*); Radopholus spp. (e.g. *R. similis;* lesion nematodes such as Pratylenchus spp. (e.g. *P. pratensis*); Belonolaimus spp. (eg, *B. gracilis*); Tylenchulus spp. (e.g. *T. semipenetrans*); Rotylenchulus spp. (e.g. *R. reniformis*); Rotylenchus spp. (*R. robustus*); Helicotylenchus spp. (e.g. *H. multicinctus*); Hemicycliophora spp. (e.g. *H. gracilis*); Criconemoides spp. (e.g. *C. similis*); Trichodorus spp. (e.g. *T. primitivus*); dagger nematodes such as Xiphinema spp. (e.g. *X. diversicaudatum*), Longidorus spp. (e.g. *L. elongatus*); Hoplolaimus spp. (e.g. *H. coronatus*): Aphelenchoides spp. (e.g *A. ritzema-bosi, A. besseyi*); stem and bulb eelworm such as Ditylenchus spp. (e.g. *D. dipsaci*).

In the field of veterinary medicine or livestock husbandry or in the maintenance of public health against arthropods, helminths or protozoa which are parasitic internally or externally upon vertebrates, particularly warm-blooded vertebrates, for example man or domestic animals, e.g. cattle, sheep, goats, equines, swine, poultry, dogs or cats, for example Acarina, including ticks (e.g. Ixodes spp., Boophilus spp. e.g. *Boophilus microplus,* Amblyomma spp., Hyalomma spp., Rhipicephalus spp. e.g. *Rhipicephalus appendiculatus,* Haemaphysalis spp., Dermacentor spp., Ornithodorus spp. (e.g. *Ornithodorus moubata*) and mites (e.g. Damalinia spp., *Dermahyssus gallinae,* Sarcoptes spp. e.g. *Sarcoptes scabiei,* Psoroptes spp., Chorioptes spp;, Demodex spp., Eutrombicula spp.,); Diptera (e.g. Aedes spp., Anopheles spp., Musca spp., Hypoderma spp., Gasterophilus spp., Simulium spp); Hemiptera (e.g. Triatoma spp); Phthirapter (e.g. Damalinia spp., Linognathus spp.); Siphonaptera (e.g. Ctenocephalides spp.); Dictyoptera (e.g. Periplaneta spp., Blatella spp.); Hymenoptera (e.g. *Monomorium pharaonis*); for example against infections of the gastro-intestinal tract caused by parasitic nematode worms, for example members of the family Trichostrongylidae, *Nippostrongylus brasiliensis, Trichinella spiralis, Haemonchus contortus, Trichostrongylus colubriformis, Nematodirus batus, Ostertagis circumcincta, Trichostrongylus axei,* Cooperia spp. and *Hymenolepis nana;* in the control and treatment of protozoal diseases caused by, for example, Eimeria spp. e.g. *Eimeria tenella, Eimeria acervulina, Eimeria brunetti, Eimeria maxima* and *Eimeria necatrix, Tryanosoms cruzi,* Leishaminia spp., Plasmodium spp., Babesis spp., Trichomonadidae spp., Histomanas spp., Giardia spp., Toxoplasma spp., *Entamoeba histolytica* and Theileria spp..

The invention, as previously described, provides methods of control of pests via application or administration of an effective amount of compounds of formula (I) or (Ia) at a locus which composes treatment of the locus.

In practical use for the control of arthropods, especially insects or mites, or nematode pests of plants, a method, for example, comprises applying to the plants or to the medium in which they grow an effective amount of a compound of the invention. For such a method, the active compound is generally applied to the locus in which the arthropod or nematode infestation is to be controlled at an effective rate in the range of about 0.005 kg to about 15 kg of the active compound per hectare of locus treated. Under ideal conditions, depending on the pest to be controlled, a lower rate may offer adequate protection. On the other hand, adverse weather conditions, resistance of the pest or other factors may require that the active ingredient be used at higher rates. The optimum rate depends usually upon a number of factors, for example, the type of pest being controlled. the type or the growth stage of the infested plant, the row spacing or also the method of application. More preferably an effective rate range of the active compound is from about 0.01 kg/ha to about 2 kg/ha.

When a pest is soil-borne, the active compound generally in a formulated composition, is distributed evenly over the area to be treated (ie, for example broadcast or band treatment) in any convenient manner. Application may be made, if desired, to the field or crop-growing area generally or in close proximity to the seed or plant to be protected from attack. The active component can be washed into the soil by spraying with water over the area or can be left to the natural action of rainfall. During or after application, the formulated compound can, if desired, be distributed mechanically in the soil, for example by ploughing, disking, or use of drag chains. Application can be prior to planting, at planting, after planting but before sprouting has taken place, or after sprouting. Additionally, a method of control may also comprise treatment of the seed prior to planting with subsequent control effected after planting the seed.

Methods of control of pests also consist of application to or treatment of the foliage of plants to control arthropods, especially insects or mites, or nematodes attacking the aerial parts of the plants. In addition, methods of control of pests by the invention compounds are provided to control pests which feed on parts of the plant remote from the point of application. e.g., leaf feeding insects which are controlled via systemic action of the active compound when applied for example to the roots of a plant or to the plant seed prior to planting. Furthermore, the compounds of the invention may reduce attacks on a plant by means of antifeeding or repellent effects.

The compounds of the invention and methods of control of pests therewith are of particular value in the protection of field, forage, plantation, glasshouse, orchard or vineyard crops, of ornamentals, or of plantation or forest trees, for example: cereals (such as maize, wheat, rice, or sorghum), cotton, tobacco, vegetables (such as beans, cole crops, curcurbits, lettuce, onions, tomatoes or peppers), field crops (such as potatoes, sugar beets, ground nuts, soybeans, or oil seed rape), sugar cane, grassland or forage crops (such as maize, sorghum, or lucerne), plantations (such as tea, coffee, cocoa, banana, palm oil, coconut, rubber, or spices), orchards or groves (such as of stone or pit fruit, citrus, kiwifruit, avocado, mango, olives or walnuts), vineyards, ornamental plants, flowers or vegetables or shrubs under glass or in gardens or parks, or forest trees (both deciduous and evergreen) in forests, plantations or nurseries.

They are also valuable in the protection of timber (standing, felled, converted, stored or structural) from attack, for example, by sawflies or beetles or termites.

They have applications in the protection of stored products such as grains, fruits, nuts, spices or tobacco, whether whole, milled or compounded into products, from moth, beetle, mite or grain weevil attack. Also protected are stored animal products such as skins, hair, wool or feathers in natural or converted form (e.g. as carpets or textiles) from moth or beetle attack as well as stored meat, fish or grains from beetle, mite or fly attack.

Additionally, the compounds of the invention and methods of use thereof are of particular value in the control of arthropods, helminths or protozoa which are injurious to, or spread or act as vectors of diseases in man and domestic animals, for example those hereinbefore mentioned, and more especially in the control of ticks, mites, lice, fleas, midges, or biting, nuisance or myiasis flies. The compounds of the invention are particularly useful in controlling arthropods, helminths or protozoa which are present inside domestic host animals or which feed in or on the skin or suck the blood of the animal, for which purpose they may be administered orally, parenterally, percutaneously or topically.

Furthermore, compounds of the invention may be useful for coccidiosis, a disease caused by infections from protozoan parasites of the genus Eimeria. It is an important potential cause of economic loss in domestic animals and birds, particularly those raised or kept under intensive conditions. For example, cattle, sheep, pigs or rabbits may be affected, but the disease is especially important in poultry, particularly in chickens. Administration of a small-amount of a compound of the invention, preferably by a combination with feed is effective in preventing or greatly reducing the incidence of coccidiosis. The compounds are effective against both the cecal form and the intestinal forms. Furthermore, the compounds of the invention may also exert an inhibiting effect on oocytes by greatly reducing the number and sporulation of those produced. The poultry disease is generally spread by the birds picking up the infectious organism in droppings in or on contaminated litter, ground, food, or drinking water. The disease is manifested by hemorrhage, accumulation of blood in the ceca, passage of blood to the droppings, weakness and digestive disturbances. The disease often terminates in the death of the animal, but the fowl which survive severe infections have had their market value subtantially reduced as a result of the infection.

The compositions hereinafter described for application to growing crops or crop growing loci or as a seed dressing may, in general, alteratively be employed for topical application to man or animals or in the protection of stored products, household goods, property or areas of the general environment. Suitable means of applying the compounds of the invention include:

to growing crops as foliar sprays, dusts, granules, fogs or foams or also as suspensions of finely divided or encapsulated compositions as soil or root treatments by liquid drenches, dusts, granules, smokes or foams; to seeds of crops via application as seed dressings by liquid slurries or dusts;

to persons or animals infested by or exposed to infestation by arthropods, helminths or protozoa, by parenteral, oral or topical application of compositions in which the active ingredient exhibits an immediate and-/or prolonged action over a period of time against the arthropods, helminths or protozoa, for example by incorporation in feed or suitable orally-ingestible pharmaceutical formulations, edible baits, salt licks, dietary supplements, pour-on formulations, sprays, baths, dips, showers, jets, dusts, greases, shampoos, creams, wax smears or livestock self-treatment systems;

to the environment in general or to specific locations where pests may lurk, including stored products, timber, household goods, or domestic or industrial premises, as sprays, fogs, dusts, smokes, wax-smears, lacquers, granules or baits, or in tricklefeeds to waterways, wells, reservoirs or other running or standing water;

to domestic animals in feed to control fly larvae feeding in their feces;

In practice, the compounds of the invention most frequently form parts of compositions. These compositions can be employed to control: arthopods, especially insects or mites; nematodes; or helminth or protozoan pests. The compositions may be of any type known in the art suitable for application to the desired pest in any premises or indoor or outdoor area or by internal or external administration to vertebrates. These compositions contain at least one compound of the invention, such as described earlier, as the active ingredient in combination or association with one or more other compatible components which are for example, solid or liquid carriers or diluents, adjuvants, surface-active-agents, or the like appropriate for the intended use and which are agronomically or medicinally acceptable. These compositions, which may be prepared by any manner known in the art, likewise form a part of this invention.

These compositions may also contain other kinds of ingredients such as protective colloids, adhesives, thickeners, thixotropic agents, penetrating agents, spray oils (especially for acaridical use), stabilizers, preservative agents (especially mold preservatives), sequestering agents, or the like, as well as other known active ingredients with pesticidal properties (particularly insecticidal, miticidal, nematicidal, or fungicidal) or with properties regulating the growth of plants. More generally, the compounds employed in the invention may be combined with all the solid or liquid additives corresponding to the usual techniques of formulation.

Compositions, suitable for applications in agriculture, horticulture, or the like include formulations suitable for use as, for example, sprays, dusts, granules, fogs, foams, emulsions, or the like.

Compositions suitable for administration to vertebrates or man, include preparations suitable for oral, parenteral, percutaneous, e.g. pour-on, or topical administration.

Compositions for oral administration comprise one or more of the compounds of general formula(I) in association with pharmaceutically acceptable carriers or coatings and include, for example, tablets, pills, capsules, pastes, gels, drenches, medicated feeds, medicated drinking water, medicated dietary supplements, slow-release boluses or other slow-release devices intended to be retained within the gastro-intestinal tract. Any of these may incorporate the active ingredient contained within microcapsules or coated with acid-labile or alkali-labile or other pharmaceutically acceptable enteric coatings. Feed premixes or concentrates containing compounds of the present invention for use in preparation of medicated diets, drinking water or other materials for consumption by animals may also be used.

Compositions for parenteral administration include solutions, emulsions or suspensions in any suitable pharmaceutically acceptable vehicle or solid or semisolid subcutaneous implants or pellets designed to release the active ingredient over a protracted period of time and may be prepared and made sterile in any appropriate manner known to the art.

Compositions for percutaneous and topical administration include sprays, dusts, baths, dips, showers, jets, greases, shampoos, creams, wax-smears, or pour-on preparations or devices (e.g. ear tags attached externally to animals in such a way as to provide local or systemic arthropod control).

Solid or liquid baits, suitable for controlling arthropods, comprise one or more compounds of general formula(I) and a carrier or diluent which may include a food substance or some other substance to induce consumption by the arthropod.

The effective use doses of the compounds employed in the invention can vary within wide limits, particularly depending on the nature of the pest to be eliminated or degree of infestation, for example, of crops with these pests. In general, the compositions according to the invention usually contain about 0.05 to about 95% (by weight) of one or more active ingredients according to the invention, about 1 to about 95% of one or more solid or liquid carriers and, optionally, about 0.1 to about 50% of one or more other compatible components, such as surface-active agents or the like.

In the present account, the term "carrier" denotes an organic or inorganic ingredient, natural or synthetic, with which the active ingredient is combined to facilitate its application, for example, to the plant, to seeds or to the soil. This carrier is therefore generally inert and it must be acceptable (for example, agronomically acceptable, particularly to the treated plant).

The carrier may be a solid, for example, clays, natural or synthetic silicates, silica, resins, waxes, solid fertilizers (for example ammonium salts), ground natural minerals, such as kaolins, clays, talc, chalk, quartz, attapulgite, montmorillonite, bentonite or diatomaceous earth, or ground synthetic minerals, such as silica, alumina, or silicates especially aluminium or magnesium silicates. As solid carriers for granules the following are suitable: crushed or fractionated natural rocks such as calcite, marble, pumice, sepiolite and dolomite; synthetic granules of inorganic or organic meals; granules of organic material such as sawdust, coconut shells, corn cobs, corn husks or tobacco stalks; kieselguhr, tricalcium phosphate, powdered cork, or absorbent carbon black; water soluble polymers, resins, waxes; or solid fertilizers. Such solid compositions may, if desired, contain one or more compatible wetting, dispersing, emulsifying or colouring agents which, when solid, may also serve as a diluent.

The carrier may also be liquid, for example: water; alcohols, particularly butanol or glycol, as well as their ethers or esters, particularly methylglycol acetate; ketones, particularly acetone, cyclohexanone, methylethyl ketone, methylisobutylketone, or isophorone; petroleum fractions such as paraffinic or aromatic hydrocarbons, particularly xylenes or alkyl naphthalenes; mineral or vegetable oils; aliphatic chlorinated hydrocarbons, particularly trichloroethane or methylene chloride; aromatic chlorinated hydrocarbons, particularly chlorobenzenes; water-soluble or strongly polar solvents such as dimethylformamide, dimethyl sulphoxide, or N-methylpyrrolidone; liquefied gases; or the like or a mixture thereof.

The surface-active agent may be an emulsifying agent, dispersing agent or wetting agent of the ionic or non-ionic type or a mixture of such surface-active agents. Amongst these are e.g., salts of polyacrylic acids, salts of lignosulphonic acids, salts of phenolsulphonic or naphthalenesulphonic acids, polycondensates of ethylene oxide with fatty alcohols or fatty acids or fatty esters or fatty amines, substituted phenols (particularly alkylphenols or arylphenols), salts of sulphosuccinic acid esters, taurine derivatives (particularly alkyltaurates), phosphoric esters of alcohols or of polycondensates of ethylene oxide with phenols, esters of fatty acids with polyols, or sulphate, sulphonate or phosphate functional derivatives of the above compounds. The presence of at least one surface-active agent is generally essential when the active ingredient and/or the inert carrier are only slightly water soluble or are not water soluble and the carrier agent of the con, position for application is water.

Compositions of the invention may further contain other additives such as adhesives or colorants. Adhesives such as carboxymethylcellulose or natural or synthetic polymers in the form of powders, granules or lattices, such as arabic gum, polyvinyl alcohol or polyvinyl acetate, natural phospholipids, such as cephalins or lecithins, or synthetic phospholipids can be used in the formulations. It is possible to use colorants such as inorganic pigments, for example: iron oxides, titanium oxides or Prussian Blue; organic dyestuffs, such as alizarin dyestuffs, azo dyestuffs or metal phthalocyanine dyestuffs; or trace nutrients such as salts of iron, manganese, boron, copper, cobalt, molybdenum or zinc.

Compositions containing compounds of general formula (I) which may be applied to control arthropod, plant nematode, helminth or protozoan pests, may also contain synergists (e.g. piperonyl butoxide or sesamex), stabilizing substances, other insecticides, acaricides, plant nematocides, anthelmintics or anticoccidials, fungicides (agricultural or veterinary as appropriate, e.g. benomyl and iprodione), bactericides, arthropod or vertebrate attractants or repellents or pheromones, deodorants, flavouring agents, dyes, or auxiliary therapeutic agents, e.g. trace elements. These may be designed to improve potency, persistence, safety, uptake where desired, spectrum of pests controlled or to enable the composition to perform other useful functions in the same animal or area treated.

Examples of other pesticidally-active compounds which may be included in, or used in conjunction with the compositions of the present invention are: acephate, chlorpyrifos, demeton-S-methyl, disulfoton, ethoprofos, fenitrothion, fenamiphos, fonofos, isazophos, isofenphos, malathion, monocrotophos, parathion, phorate, phosalone, pirimiphosmethyl, terbufos, triazophos, cyfluthrin, cypermethrin, deltamethrin, fenpropathrin, fenvalerate, permethrin, tefluthrin, aldicarb, carbosulfan, methomyl, oxamyl, pirimicarb, bendiocarb, teflubenzuron, dicofol, endosulfan, lindane, benzoximate, cartap, cyhexatin, tetradifon, avermectins, ivermectins, milbemycins, thiophanate, trichlorfon, dichlorvos, diaveridine or dimetriadazole.

For their agricultural application, the compounds of the formula(I) are therefore generally in the form of compositions, which are in various solid or liquid forms.

Solid forms of compositions which can be used are dusting powders (with a content of the compound of formula(I) ranging up to 80%), wettable powders or granules (including water dispersible granules), particularly those obtained by extrusion, compacting, impregnation of a granular carrier, or granulation starting from a powder (the content of the compound of formula(I) in these wettable powders or granules being between about 0.5 and about 80%). Solid homogenous or heterogenous compositions containing one or more compounds of general formula(I) for example granules, pellets, briquettes or capsules, may be used to treat standing or running water over a period of time. A similar effect may be achieved using trickle or intermittent feeds of water dispersible concentrates as described herein.

Liquid compositions, for example, include aqueous or non-aqueous solutions or suspensions (such as emulsifiable concentrates, emulsions, flowables, dispersions, or solutions) or aerosols. Liquid compositions also include, in particular, emulsifiable concentrates, dispersions, emulsions, flowables, aerosols, wettable powders (or powder for spraying), dry flowables or pastes as forms of compositions which are liquid or intended to form liquid compositions when applied, for example as aqueous sprays (including low and ultra-low volume) or as fogs or aerosols.

Liquid compositions, for example, in the form of emulsifiable or soluble concentrates most frequently comprise about 5 to about 80% by weight of the active ingredient, while the emulsions or solutions which are ready for application contain, in their case, about 0.01 to about 20% of the active ingredient. Besides the solvent, the emulsifiable or soluble concentrates may contain, when required, about 2 to about 50% of suitable additives, such as stabilizers, surface-active agents, penetrating agents, corrosion inhibitors, colorants or adhesives. Emulsions of any required concentration, which are particularly suitable for application, for example, to plants, may be obtained from these concentrates by dilution with water. These compositions are included within the scope of the compositions which may be employed in the present invention. The emulsions may be in the form of water-in-oil or oil-in-water type and they may have a thick consistency.

The liquid compositions of this invention may, in addition to normal agricultural use applications be used for example to treat substrates or sites infested or liable to infestation by arthropods (or other pests controlled by compounds of this invention) including premises, outdoor or indoor storage or processing areas, containers or equipment or standing or running water.

All these aqueous dispersions or emulsions or spraying mixtures can be applied, for example, to crops by any suitable means, chiefly by spraying, at rates which are generally of the order of about 100 to about 1,200 liters of spraying mixture per hectare, but may be higher or lower (eg. low or ultra-low volume) depending upon the need or application technique. The compounds or compositions according to the invention are conveniently applied to vegetation and in particular to roots or leaves having pests to be eliminated. Another method of application of the compounds or compositions according to the invention is by chemigation, that is to say, the addition of a formulation containing the active ingredient to irrigation water. This irrigation may be sprinkler irrigation for foliar pesticides or it can be ground irrigation or underground irrigation for soil or for systemic pesticides.

The concentrated suspensions, which can be applied by spraying, are prepared so as to produce a stable fluid product which does not settle (fine grinding) and usually contain from about 10 to about 75% by weight of active ingredient, from about 0.5 to about 30% of surface-active agents, from about 0.1 to about 10% of thixotropic agents, from about 0 to about 30% of suitable additives, such as anti-foaming agents, corrosion inhibitors, stabilizers, penetrating agents, adhesives and, as the carrier, water or an organic liquid in which the active ingredient is poorly soluble or insoluble. Some organic solids or inorganic salts may be dissolved in the carrier to help prevent settling or as antifreezes for water.

The wettable powers (or powder for spraying) are usually prepared so that they contain from about 10 to about 80% by weight of active ingredient, from about 20 to about 90% of a solid carrier, from about 0 to about 5% of a wetting agent, from about 3 to about 10% of a dispersing agent and, when necessary, from about 0 to about 80% of one or more stabilizers and/or other additives, such as penetrating agents, adhesives, anti-caking agents, colorants, or the like. To obtain these wettable powders, the active ingredient(s) is(are) thoroughly mixed in a suitable blender with additional substances which may be impregnated on the porous filler and is(are) ground using a mill or other suitable grinder. This produces wettable powders, the wettability and the suspendability of which are advantageous. They may be suspended in water to give any desired concentration and this suspension can be employed very advantageously in particular for application to plant foliage.

The "water dispersible granules (WG)" (granules which are readily dispersible in water) have compositions which are substantially close to that of the wettable powders. They may be prepared by granulation of formulations described for the wettable powders, either by a wet route (contacting finely divided active ingredient with the inert filler and a little water, e.g. 1 to 20% by weight, or with an aqueous solution of a dispersing agent or binder, followed by drying and screening), or by a dry route (compacting followed by grinding and screening).

The application dose (effective dose) of active ingredient, also as a formulated composition, is generally between about 0.005 and about 15 kg/ha, preferably between about 0.01 and about 2 kg/ha. Therefore, the rates and concentrations of the formulated compositions may vary according to the method of application or the nature of the compositions or use thereof. Generally speaking, the compositions for application to control arthropod, plant nematode, helminth or protozoan pests usually contain from about 0.00001% to about 95%, more particularly from about 0.0005% to about 50% by weight of one or more compounds of general formula(I) or of total active ingredients (that is to say the compound(s) of general formula(I) together with: other substances toxic to arthropods or plant nematodes, anthelmintics, anticoccidials, synergists, trace elements or stabilizers). The actual compositions employed and their rate of application will be selected to achieve the desired effect(s) by the farmer, livestock producer, medical or veterinary practitioner, pest control operator or other person skilled in the art.

Solid or liquid compositions for application topically to animals, timber, stored products or household goods usually contain from about 0.00005% to about 90%, more particularly from about 0.001% to about 10%, by weight of one or more compounds of general formula(I). For administration to animals orally or parenterally, including percutaneously solid or liquid compositions, these normally contain from about 0.1% to about 90% by weight of one or more compounds of general formula(I). Medicated feedstuffs normally contain from about 0.001% to about 3% by weight of one or more compounds of general formula(I). Concentrates or supplements for mixing with feedstuffs normally contain from about 5% to about 90%, preferably from about 5% to about 50%, by weight of one or more compounds of general formula(I). Mineral salt licks normally contain from about 0.1% to about 10% by weight of one or more compounds of general formula(I).

Dusts or liquid compositions for application to livestock, persons, goods, premises or outdoor areas may contain from about 0.0001% to about 15%, more especially from about 0.005% to about 2.0%, by weight, of one or more compounds of general formula(I). Suitable concentrations in treated waters are between about 0.0001 ppm and about 20 ppm, more particularly about 0.001 ppm to about 5.0 ppm. of one or more compounds of general formula(I) and may be used therapeutically in fish farming with appropriate exposure times. Edible baits may contain from about 0.01% to about 5%, preferably from about 0.01% to about 1.0%, by weight, of one or more compounds of general formula(I).

When administered to vertebrates parenterally, orally or by percutaneous or other means, the dosage of compounds of general formula(I) will depend upon the species, age, or health of the vertebrate and upon the nature and degree of its actual or potential infestation by arthropod, helminth or protozoan pests. A single dose of about 0.1 to about 100 mg, preferably about 2.0 to about 20.0 mg, per kg body weight of the animal or doses of about 0.01 to about 20.0 mg, preferably about 0.1 to about 5.0 mg, per kg body weight of the animal per day, for sustained medication, are generally suitable by oral or parenteral administration. By use of sustained release formulations or devices, the daily doses required over a period of months may be combined and administered to animals on a single occasion.

The following composition EXAMPLES 7A–7L illustrate compositions for use against arthropods, especially mites or insects, plant nematodes, or helminth or protozoan pests which comprise, as active ingredient, compounds of general formula (I), especially compounds according to formula (Ia), such as those described in preparative examples. The compositions described in EXAMPLES 7A–7F can each be diluted in water to give a sprayable compositon at concentrations suitable for use in the field. Generic chemical descriptions of the ingredients (for which all of the following percentages are in weight percent), used in the composition EXAMPLES 7A–7L exemplified below, are as follows:

| Trade Name | Chemical Description |
|---|---|
| Ethylan BCP | Nonylphenol ethylene oxide condensate |
| Soprophor BSU | Tristyrylphenol ethylene oxide condensate |
| Arylan CA | A 70% w/v solution of calcium dodecylbenzenesulfonate |
| Solvesso 150 | Light $C_{10}$ aromatic solvent |
| Arylan S | Sodium dodecylbenzenesulfonate |
| Darvan No2 | Sodium lignosulphonate |
| Celite PF | Synthetic magnesium silicate carrier |
| Sopropon T36 | Sodium salts of polycarboxylic acids |
| Rhodigel 23 | Polysaccharide xanthan gum |
| Bentone 38 | Organic derivative of magnesium montmorillonite |
| Aerosil | Microfine silicon dioxide |

EXAMPLE 7A

A water soluble concentrate is prepared with the composition as follows:

| Active ingredient | 7% |
|---|---|
| Ethylan BCP | 10% |
| N-methylpyrrolidone | 83% |

To a solution of Ethylan BCP dissolved in a portion of N-methylpyrrolidone is added the active ingredient with heating and stirring until dissolved. The resulting solution is made up to volume with the remainder of the solvent.

EXAMPLE 7B

An emulsifiable concentrate (EC) is prepared with the composition as follows:

| Active ingredient | 7% |
|---|---|
| Soprophor BSU | 4% |
| Arylan CA | 4% |
| N-methylpyrrolidone | 50% |
| Solvesso 150 | 35% |

The first three composition are dissolved in N-methylpyrrolidone and to this is then added the Solvesso 150 to give the final volume.

EXAMPLE 7C

A wettable powder (WP) is prepared with the composition as follows:

| Active ingredient | 40% |
|---|---|
| Arylan S | 2% |
| Darvan No 2 | 5% |
| Celite PF | 53% |

The ingredients are mixed and ground in a hammermill to a powder with a particle size of less than 50 microns.

EXAMPLE 7D

An aqueous-flowable formulation is prepared with the composition as follows:

| Active ingredient | 40.00% |
|---|---|
| Ethylan BCP | 1.00% |
| Sopropon T360. | 0.20% |
| Ethylene glycol | 5.00% |
| Rhodigel 230. | 0.15% |
| Water | 53.65% |

The ingredients are intimately mixed and are ground in a bead mill until a mean particle size of less than 3 microns is obtained.

EXAMPLE 7E

An emulsifiable suspension concentrate is prepared with the composition as follows:

| Active ingredient | 30.0% |
|---|---|
| Ethylan BCP | 10.0% |
| Bentone 38 | 0.5% |
| Solvesso 150 | 59.5% |

The ingredients are intimately mixed and ground in a beadmill until a mean particle size of less than 3 microns is obtained.

EXAMPLE 7F

A water dispersible granule is prepared with the composition as follows:

| | |
|---|---|
| Active ingredient | 30% |
| Darvan No 2 | 15% |
| Arylan S | 8% |
| Celite PF | 47% |

The ingredients are mixed, micronized in a fluid-energy mill and then granulated in a rotating pelletizer by spraying with water (up to 10%). The resulting granules are dried in a fluid-bed drier to remove excess water.

EXAMPLE 7G

A dusting powder is prepared with the composition as follows:

| | |
|---|---|
| Active ingredient | 1 to 10% |
| Talc powder-superfine | 99 to 90% |

The ingredients are intimately mixed and further ground as necessary to achieve a fine powder. This powder may beapppplied to a locus of arthropod infestation, for example refuse dumps, stored products or household goods or animals infested by, or at risk of infestation by, arthropods to control the arthropods by oral ingestion. Suitable means for distributing the dusting powder to the locus of arthropod infestation include mechanical blowers, handshakers or livestock self treatment devices.

EXAMPLE 7H

An edible bait is prepared with the composition as follows:

| | |
|---|---|
| Active ingredient | 0.1 to 1.0% |
| Wheat flour | 80% |
| Molasses | 19.9 to 19% |

The ingredients are intimately mixed and formed as required into a bait form. This edible bait may be distributed at a locus, for example domestic or industrial premises, e.g. kitchens, hospitals or stores, or outdoor areas, infested by arthropods, for example ants, locusts, cockroaches or flies, to control the arthropods by oral ingestion.

EXAMPLE 7I

A solution formulation is prepared with a composition as follows:

| | |
|---|---|
| Active ingredient | 15% |
| Dimethyl sulfoxide | 85% |

The active ingredient is dissolved in dimethyl sulfoxide with mixing and or heating as required. This solution may be applied percutaneously as a pour-on application to domestic animals infested by arthropods or, after sterilization by filtration through a polytetrafluoroethylene membrane (0.22 micrometer pore size), by parenteral injection, at a rate of application of from 1.2 to 12 ml of solution per 100 kg of animal body weight.

EXAMPLE 7J

A wettable powder is prepared with the composition as follows:

| | |
|---|---|
| Active ingredient | 50% |
| Ethylan BCP | 5% |
| Aerosil | 5% |
| Celite PF | 40% |

The Ethylan BCP is absorbed onto the Aerosil which is then mixed with the other ingredients and ground in a hammer-mill to give a wettable powder, which may be diluted with water to a concentration of from 0.001% to 2% by weight of the active compound and applied to a locus of infestation by arthropods, for example, dipterous larvae or plant nematodes, by spraying, or to domestic animals infested by, or at risk of infection by arthropods, helminths or protozoa, by spraying or dipping, or by oral administration in drinking water, to control the arthropods, helminths or protozoa.

EXAMPLE 7K

A slow release bolus composition is formed from granules containing the following components in varying percentages(similar to those described for the previous compositions) depending upon need:
Active ingredient
Density agent
Slow-release agent
Binder The intimately mixed ingredients are formed into granules which are compressed into a bolus with a specific gravity of 2 or more. This can be administered orally to ruminant domestic animals for retention within the reticulo-rumen to give a continual slow release of active compound over an extended period of time to control infestation of the ruminant domestic animals by arthropods, helminths or protozoa.

EXAMPLE 7L

A slow release composition in the form of granules, pellets, brickettes or the like can be prepared with compositions as follows:

| | |
|---|---|
| Active ingredient | 0.5 to 25% |
| Polyvinyl chloride | 75 to 99.5% |
| Dioctyl phthalate (plasticizer) | catalytic amount |

The components are blended and then formed into suitable shapes by melt-extrusion or molding. These composition are useful, for example, for addition to standing water or for fabrication into collars or eartags for attachment to domestic animals to control pests by slow release.

While the present invention has been set forth in specific and illustrative details and described with preferred particularity, it is susceptible to changes, modifications or alternations, obvious to one of ordinary skill in the art, without departing from the scope and spirit of the invention, which is defined by the claims appended hereto.

What we claim is:
1. A pesticidal compound of formula (I)

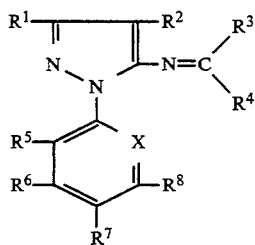

wherein:

R[1] is cyano, nitro, halogen, formyl, alkylcarbonyl or cycloalkylcarbonyl; and wherein the alkyl moieties are linear or branched chains of 1–4 carbon atoms and the cycloalkyl moiety contains 3 to 7 carbon atoms;

R[2] is: halogen; alkyl; haloalkyl; alkoxy; haloalkoxy; nitro; thiocyanato; unsubstituted or mono-or dialkyl substituted sulfamoyl; unsubstituted or mono- or dialkyl substituted aminocarbonyl; alkoxycarbonyl; or unsubstituted or substituted $R^9S(O)_n$, in which n is 0, 1 or 2 and R[9] is alkyl, haloalkyl, cycloalkyl, halocycloalkyl, cycloalkylalkyl or halocycloalkylalkyl; and wherein the alkyl moieties are linear or branched chains of 1–4 carbon atoms, the cycloalkyl moiety contains 3 to 7 carbon atoms and the halo substitution consists of one or more halogen atoms, which are the same or different, up to full substitution of the alkyl and cycloalkyl moieties;

R[3] is hydrogen, $C_{1-4}$ alkyl, $C_{1-4}$ alkoxy, $C_{1-4}$ alkylthio or di-$C_{1-4}$ alkylamino; and wherein the alkyl moieties are linear or branched chains;

R[4] is unsubstituted or substituted 5 membered monocyclic ring containing a nitrogen and 1 and 2 of the same or different of oxygen, sulfur or nitrogen atoms; and wherein substitution is one or more or combinations of: hydroxy or inorganic or organic salt thereof; sulfhydryl or inorganic or organic salt thereof; halogen; cyano; nitro; alkyl; haloalkyl; alkoxy; -O-alkyl-O-; O-haloalkyl-O-; haloalkoxy; alkanoyloxy; phenoxy; trialkylsilyloxy; phenyl; alkyl-$S(O)_n$ or haloalkyl-$S(O)_n$, in which n is 0, 1 or 2; $NR^{10}R^{11}$ in which $R^{10}$ and $R^{11}$ are individually hydrogen, alkyl, alkanoyl or haloalkanoyl; $COR^{12}$ in which $R^{12}$ is $NR^{10}R^{11}$, alkoxy, alkylthio, hydroxy or inorganic or organic salt thereof, hydrogen, alkyl or haloalkyl; or $SO_2R^{13}$ in which $R^{13}$ is $NR^{10}R^{11}$, alkoxy, alkylthio, or hydroxy or inorganic or organic salt thereof; and wherein the alkyl and alkoxy moieties are linear or branched chains of 1–4 carbon atoms and the halo substitution consists of one or more halogen atoms, which are the same or different, up to full substitution of the alkyl and alkoxy moieties;

R[5] is hydrogen, halogen or linear or branched chain $C_{1-4}$ alkyl;

R[6] and R[8] are each individually hydrogen or fluorine;

R[7] is halogen, alkyl, haloalkyl, alkoxy, haloalkoxy, cyano, nitro, alkylcarbonyl, haloalkylcarbonyl, alkyl-$S(O)_n$ or haloalkyl-$S(O)_n$ in which n is 0,1 or 2; and wherein the alkyl and alkoxy moieties are linear or branched chains of 1–4 carbon atoms and the halo substitution consists of one or more halogen atoms, which are the same or different, up to full substitution of the alkyl and alkoxy moieties; and X is a nitrogen atom (N) or C-$R^{14}$ in which $R^{14}$ is hydrogen, halogen, cyano, nitro, $C_{1-4}$ alkyl, $C_{1-4}$ alkylthio or $C_{1-4}$ alkoxy; and the alkyl moieties are linear or branched chains.

2. The pesticidal compound of claim 1 of formula (I), wherein:

R[1] is cyano, nitro or halogen;

R[2] is unsubstituted or substituted $R^9S(O)_n$, in which n is 0, 1 or 2 and R[9] is alkyl or haloalkyl as defined;

R[3] is hydrogen;

R[4] is unsubstituted or substituted imidazolyl or triazolyl;

R[5] is hydrogen, halogen or alkyl;

R[6] and R[8] are each individually hydrogen or fluorine;

R[7] is halogen, alkyl, haloalkyl or haloalkoxy; and

X is a nitrogen atom (N) or C-$R^{14}$ in which $R^{14}$ is hydrogen, halogen, cyano, alkyl, alkylthio or alkoxy.

* * * * *